(12) United States Patent
Synowiec et al.

(10) Patent No.: US 11,857,566 B2
(45) Date of Patent: Jan. 2, 2024

(54) SULFONATED POLYSTYRENE DERIVATIVE FOR USE IN THE TREATMENT AND/OR PROPHYLAXIS OF CAT FLU

(71) Applicant: UNIWERSYTET JAGIELLONSKI, Cracow (PL)

(72) Inventors: Aleksandra Synowiec, Cracow (PL); Magdalena Pachota, Cracow (PL); Krzysztof Pyrc, Cracow (PL); Maria Nowakowska, Cracow (PL); Krzysztof Szczubialka, Krzywaczka (PL)

(73) Assignee: UNIWERSYTET JAGIELLONSKI, Cracow (PL)

( * ) Notice: Subject to any disclaimer, the term of this patent is extended or adjusted under 35 U.S.C. 154(b) by 292 days.

(21) Appl. No.: 17/298,777

(22) PCT Filed: Dec. 3, 2019

(86) PCT No.: PCT/PL2019/050071
§ 371 (c)(1),
(2) Date: Jun. 1, 2021

(87) PCT Pub. No.: WO2020/117080
PCT Pub. Date: Jun. 11, 2020

(65) Prior Publication Data
US 2022/0175824 A1 Jun. 9, 2022

(30) Foreign Application Priority Data
Dec. 3, 2018 (PL) .......... 428024
Jan. 15, 2019 (PL) .......... 428583

(51) Int. Cl.
*A61K 31/795* (2006.01)
*A61P 31/22* (2006.01)
*A61P 31/14* (2006.01)
*A61K 45/06* (2006.01)

(52) U.S. Cl.
CPC .......... *A61K 31/795* (2013.01); *A61K 45/06* (2013.01); *A61P 31/14* (2018.01); *A61P 31/22* (2018.01)

(58) Field of Classification Search
CPC ......... A61P 31/12; A61K 38/28; A61K 38/09; A61K 51/00
USPC ................ 424/1.73; 514/764, 152
See application file for complete search history.

(56) References Cited

U.S. PATENT DOCUMENTS

| | | | |
|---|---|---|---|
| 6,210,653 B1 * | 4/2001 | Bellettini | A61K 51/06 424/1.73 |
| 6,239,182 B1 * | 5/2001 | Zaneveld | A61K 31/70 514/764 |
| 2004/0142910 A1 * | 7/2004 | Vachon | A61L 15/44 424/445 |
| 2008/0063604 A1 * | 3/2008 | Claudio | A61K 41/0028 424/9.52 |
| 2009/0105195 A1 * | 4/2009 | O'Brien | A01N 25/04 514/56 |

FOREIGN PATENT DOCUMENTS

| | | | |
|---|---|---|---|
| EP | 2444095 A1 | 4/2012 | |
| FR | 2736547 * | 1/1997 | .......... A61K 9/18 |
| WO | 2006/029507 A1 | 3/2006 | |
| WO | 2013/007703 A1 | 1/2013 | |

OTHER PUBLICATIONS

International Search Report and Written Opinion, PCT/PL2019/050071, dated Apr. 24, 2020.

* cited by examiner

*Primary Examiner* — Walter E Webb
(74) *Attorney, Agent, or Firm* — Arrigo, Lee, Guttman & Mouta-Bellum LLP

(57) ABSTRACT

The present invention relates to a sulfonated polystyrene derivative of formula I for use in the treatment and/or prophylaxis of cat flu, especially infection caused by feline calicivirus or feline herpesvirus, alone or in combination therapy.

Figure 1:
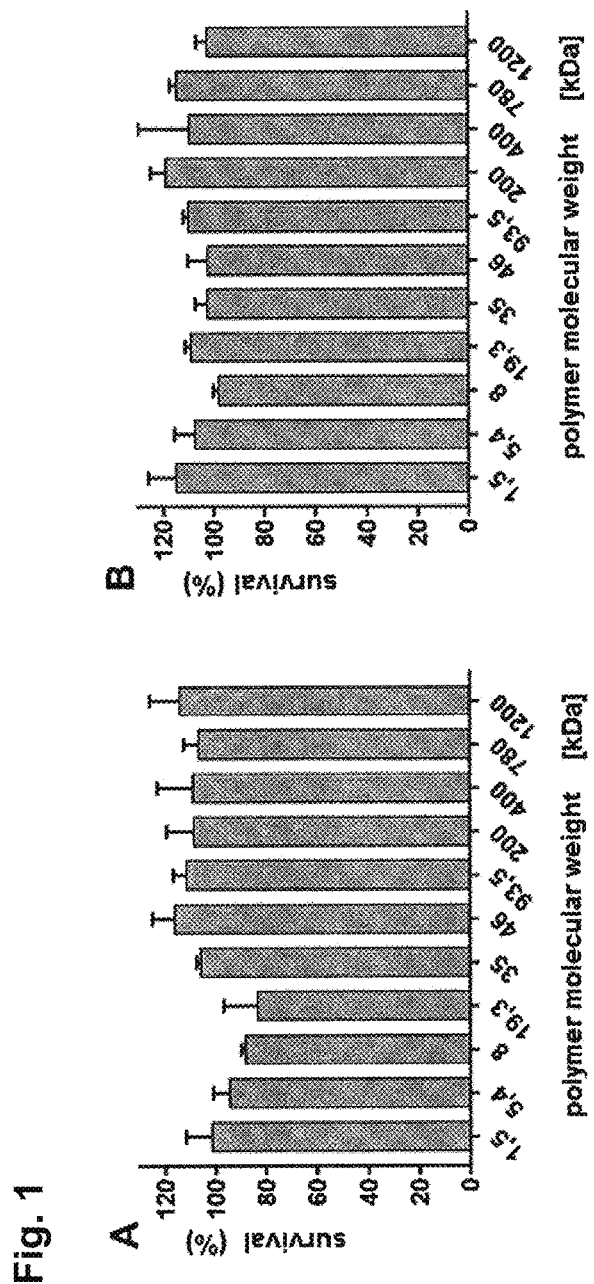

18 Claims, 16 Drawing Sheets
Specification includes a Sequence Listing.

SULFONATED POLYSTYRENE DERIVATIVE FOR USE IN THE TREATMENT AND/OR PROPHYLAXIS OF CAT FLU

Reference to Sequence Listing Submitted Electronically

The instant application contains a Sequence Listing which has been submitted electronically in ASCII format and is hereby incorporated by reference in its entirety. Said ASCII copy, created on Oct. 17, 2023, is named 17298777_ST25.txt and is 1,556 bytes in size. The present invention relates to a sulfonated polystyrene derivative, in particular sodium polystyrene sulfonate, for use in the treatment and/or prophylaxis of cat flu, in particular infection caused by feline calicivirus or feline herpesvirus, alone or in combination with other drugs.

Upper respiratory tract disease (URTD) in cats, called "cat flu", is a common disease whose symptoms include coughing, sneezing, runny nose, redness of the eyes, fever or the appearance of purulent discharge from nose and eyes [1, 2]. The disease is considered as one of the main causes of death in animal shelters and in catteries [3]. The main viral etiological factors of this disease are feline herpesvirus type 1 (FHV-1, FeHv-1) and feline calicivirus (FCV) [1, 3-5].

Feline herpesvirus type 1 (FHV-1, FeHv-1) is a member of the Herpesviridae family, which encompasses enveloped DNA viruses. Herpesviruses are pathogens that infect humans and many animal species—mammals, reptiles, birds, amphibians and fish [6]. One of the most common pathogens found in humans is herpes simplex virus type 1 (HSV-1) responsible for ulcers that occur mainly in the face, although infections are also possible in other regions of the body. Infections caused by herpesviruses can lead to the development of more severe diseases or death [6, 7]. Feline herpesvirus is related to the HSV-1 and is spread worldwide in the cat population. It is estimated that up to 90% of the cat population is seropositive for this pathogen, while in 80% the virus is present in the latent state [8, 9]. FHV-1 infections are mainly associated with upper respiratory tract inflammation, mucosal infections and eye infections (corneal ulcers, acute conjunctivitis and keratitis), which can lead to blindness [10-13]. What's more, bacterial co-infections are especially dangerous for kittens and immunocompromised individuals, as they can be fatal.

Feline herpesvirus replicates primarily in epithelial tissue and leads to acute inflammation [13]. After infection of epithelial cells, the virus is transported inside sensory neurons by retrograde route, i.e. towards the cell body, and then goes into a state of latency. The latent virus occurs in episomal form, however it may be reactivated and the disease may relapse in the event of weakening of the host's immune system [8, 14, 15].

To treat herpesviral infections in humans nucleoside analogues are currently used. Acyclovir, penciclovir, idoxuridine, cidovir and vidarabine belong to this group. These molecules inhibit viral replication by blocking the active center of viral DNA polymerase. Nucleoside analogues are delivered to the cell in an inactive form, and activation occurs as a result of phosphorylation performed by herpesvirus thymidine kinase (TK). In the next stage, there are another two phosphorylations of the molecule, carried out by host GMP kinases [16, 17]. The triphosphorylated compound can be used by the viral DNA polymerase as a substrate during the polynucleotide chain extension reaction, and once the derivative is incorporated into DNA, elongation stops. Nucleoside analogues have a much higher affinity for viral polymerase than for host polymerase [18]. Surprisingly, despite similar disease symptoms and the phylogenetic similarity of viruses, the efficacy profile of individual drugs varies in humans and cats. Some drugs that are safe and effective in humans are toxic to the cat [19-21]. For example, acyclovir (ACV) is a very effective inhibitor of HSV-1 virus replication in humans, but in cats it did not show equally high activity and its bioavailability was low [22]. Valaciclovir (VCV) is a compound transformed by hepatic esterases into ACV, which is also very often used in humans to treat herpesviral infections [23]. Despite the high antiviral activity of VCV in vitro, cats who took the drug did not improve symptoms of the disease, and in addition there were many adverse effects, such as bone marrow suppression or liver and kidney necrosis leading to animal death [24]. However, another acyclovir derivative, penciclovir (PCV), seems to be an effective and safe solution [20, 25, 26]. In addition, famciclovir, a precursor of PCV, has been tested in the treatment and prophylaxis of FHV infection in cats and has been shown to be safe [27, 28]. Famciclovir is converted to PCV by hepatic aldehyde oxidases [29, 30], transported into the cell, and, like ACV, is then phosphorylated by viral TK. Then another two phosphorylations are carried out by cellular enzymes and the polynucleotide chain extension of the genetic material of the virus is inhibited [31]. However, the concentration of PCV in cats was much lower than expected, which is probably associated with much lower activity of liver aldehyde oxidases in cats than in other mammals, so that the precursor, i.e. famciclovir, is not converted to the active form, i.e. PCV [26, 27, 32].

FCV is a member of the Caliciviridae family, which includes non-enveloped viruses containing genetic material in the form of single-stranded RNA with positive polarity. Due to the phylogenetic relationship, caliciviruses have been divided so far into five types: Lagovirus, Nebovirus, Norovirus, Sapovirus and Vesivirus [45], while in February 2019 International Committee on Taxonomy of Viruses (ICTV) formulated a new classification in which, due to the large genetic diversity of members of the Caliciviridae family, six new genera were classified (in addition to the previous five): Bavovirus, Minovirus, Nacovirus, Nebovirus, Recovirus and Valovirus. Viruses from this family can infect both humans and animals. One of the best known representatives of this family are noroviruses and sapoviruses, which cause non-bacterial gastroenteritis in mammals. Lagoviruses cause lethal hemorrhagic fever in rabbits. In cats, FCV often causes inflammation of the upper respiratory tract, especially dangerous for individuals with impaired immune system [46-48]. FCV is a pathogen found in the cat population around the world [45, 49]. It usually causes mild conjunctivitis and upper respiratory tract inflammation, however, symptoms also include ulceration and chronic stomatitis, salivation, and rarely lameness associated with acute synovitis [50-52]. FCV genetic material is single-stranded RNA, and the high genome variability means that the virus is able to adapt very quickly to changing environmental conditions [53]. Although a relatively effective vaccine against FCV exists and infections usually do not threaten the animal's life, secondary bacterial infections pose a major threat to cats [54]. In recent years, FCV strains belonging to so-called VS-FCV (virulent systemic FCV) have also been shown to appear in the cat population, which are the cause of an epidemic with a mortality rate of up to 60% in connection with multiple organ failure; according to the literature, one strain caused symptoms of hemorrhagic fever [48, 55-58]. The treatment of an infection caused by FCV is based only on antibiotic therapy, which aims at preventing secondary bacterial infections. Currently, no therapeutic agent acting directly on FCV is used in veterinary medicine. It is worth mentioning that very high in vitro antiviral activity has been demonstrated for compounds such as lithium chloride [59] and mefloquine [60]. Unfortunately, no studies on the efficacy of these compounds in cats in vivo have been performed [59, 60]. Furthermore, ribavirin, which also inhibits FCV infection in vitro, is too toxic after oral administration to be used in cats [61].

The above examples indicate that currently available agents for the treatment and/or prophylaxis of respiratory syndrome in cats that may be caused by viruses, such as FHV or FCV, are insufficiently effective and/or too toxic. There is therefore a need to find an effective therapeutic agent that will efficiently reduce the infection and transmission of both viruses, while being safe for cats.

Sulphonated polystyrene derivatives are known. Their antimicrobial properties, in particular antiviral, are also known, as well as their use in medicine, e.g. for the treatment of hyperkalemia. A representative, known sulfonated polystyrene derivative is sodium polystyrene sulfonate (poly(sodium styrenesulfonate, PSSNa)). It is known for its antibacterial and antiviral activity. It has been shown to inhibit the replication of many pathogens, including: HIV, HPV, HSV-1, HSV-2, *Gardnerella vaginalis, Chlamydia trachomatis* and *Neisseria gonorrhoeae* [33-37]. So far, however, the possibility of its use in the case of infection caused by the FCV or FHV-1 virus has not been demonstrated. In the case of HSV, the PSSNa polymer has been shown to inhibit replication by preventing virions from binding to the cell surface, which makes transmission of the virus from an infected cell to a healthy cell more difficult [35]. Considering that the proposed mechanism of action involves antiviral activity in the early stages of infection, it has been suggested that PSSNa is a heparan sulphate (HS) mimetic, i.e. it is able to "mimic" HS present on the surface of infected cells, which serves as an adhesion molecule for HSV. In addition, other heparan sulfate mimetics, such as fucosanoids, dextran sulfates and mannan sulfates, have been shown to block the binding of HSV-1 and HSV-2 viruses to adhesive agents [38-41]. Furthermore, type IV λ-carrageenans, which are also considered as HS mimetics, are able to bind FHV-1 virus, which leads to blocking its interaction with adhesion factor (HS). Despite the fact that the results obtained with the use of type IV λ-carrageenans in vitro were promising, no improvement in the health status was observed after the administration of the preparation containing this compound in cats [42].

There is a need to obtain new inhibitors of feline herpesvirus and calicivirus replication, in particular FHV-1 and FCV, especially agents with a different mechanism of action than currently available for the treatment and/or prevention of infection caused by feline herpesvirus and feline calicivirus, which would also be suitable for combination therapy for this type of infection.

The object of the invention described in the present patent application is therefore to obtain a new, effective active substance for use in the treatment and/or prophylaxis of cat flu, in particular infection caused by feline calicivirus or herpesvirus, in particular FHV-1, to obtain a new effective agent for use in treatment and/or prophylaxis of cat flu, especially infection caused by feline calicivirus or herpesvirus, which can be used in combination therapy with already available therapies for this type of infection, as well as demonstrating the possibility of using such a preparation for the treatment of this type of infection.

These goals were achieved with the solutions presented in the attached patent claims. Surprisingly, it has been found that these goals can be achieved using a sulfonated polystyrene derivative.

The present invention relates to a sulfonated polystyrene derivative of formula I:

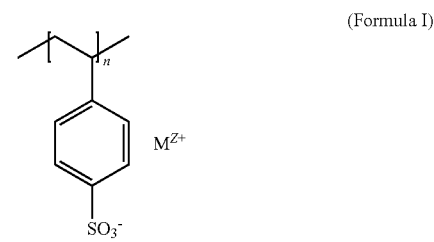

(Formula I)

wherein M is a metal cation, z is an integer from 1 to 3 and n is an integer in the range of 7 to 6000, for use in the treatment and/or prophylaxis of cat flu, especially infection caused by feline calicivirus or feline herpesvirus.

Preferably, the sulfonated polystyrene derivative to be used according to the invention is in the form of a salt, more preferably the sulfonated polystyrene derivative is in the form of a sodium salt, which is the sodium salt of polystyrene sulfonate (PSSNa).

Preferably, the sulfonated polystyrene derivative to be used according to the invention has a molecular weight of at least 1.5 kDa, more preferably at least 8 kDa.

Even more preferably, the sulfonated polystyrene derivative to be used according to the invention has a molecular weight in the range from 8 kDa to 1200 kDa, and even more preferably it has a molecular weight selected from the group consisting of 8 kDa, 19.3 kDa, 35 kDa, 46 kDa, 93.5 kDa, 200 kDa, 400 kDa, 780 kDa and 1200 kDa, most preferably it has a molecular weight of 93.5 kDa or 780 kDa.

Preferably the infection caused by feline herpesvirus or feline calicivirus is cat flu.

Preferably, the infection caused by feline herpesvirus is infection caused by feline herpesvirus type 1 (FHV-1).

Preferably, according to the invention, the sulfonated polystyrene derivative is for use in combination therapy, which preferably includes the simultaneous use of another agent for the treatment of cat flu, especially infection caused by feline calicivirus or feline herpesvirus.

By simultaneous use is meant herein to administer a compound of the invention simultaneously with another agent, preferably for the treatment of cat flu, especially infection caused by feline calicivirus or feline herpesvirus, in one formulation or in separate formulations.

More preferably, such other agent for the treatment of FHV-1 infection is a nucleoside analogue, more preferably acyclovir (ACV) and/or penciclovir (PCV).

The sulfonated polystyrene derivative according to the invention is preferably in the form of a salt, in particular a sodium salt. A representative sulfonated polystyrene derivative is sodium polystyrene sulfonate (PSSNa). An example of another polystyrene sulfonate salt may be the calcium salt or potassium salt.

Sulfonated polystyrene derivatives, such as sodium polystyrene sulfonate (PSSNa), can be prepared by any method known to those skilled in the art. These compounds may then be included in the pharmaceutical composition together with suitable pharmaceutically acceptable excipients, diluents and/or substrates. Compositions of this type can be prepared in the form of formulations suitable for administration by any route of administration, such as, for example, topical route, nasal route, or oral route. Compositions of this type may, for example, be in the form of a topical formulation, for example an ointment, or an oral formulation, for example a solution or suspension.

The compounds for use in accordance with the invention allow the prophylaxis and/or treatment of cat flu, especially infection caused by feline calicivirus or feline herpesvirus and reduce the risk of secondary infections. The compounds for use in accordance with the invention further allow the alleviation of the course of cat flu, especially infection caused by feline calicivirus or feline herpesvirus. The compounds for use in accordance with the invention are extremely effective in that they lead to almost complete inhibition of in vitro replication of viruses causing cat flu and in addition they have very low or undetectable toxicity. Furthermore, the compounds for use in accordance with the invention are suitable for use in combination therapy of cat flu, especially infection caused by feline calicivirus or feline herpesvirus, especially FHV-1, together with at least one additional agent used to treat this type of infections, especially with a different mechanism of action than the sulfonated polystyrene derivative, especially the sodium salt of polystyrene sulfonate. Examples of such other agents used to treat this type of infection are nucleoside analogues. The compounds for use in accordance with the invention are particularly suitable for use together with penciclovir (PCV). This combined use of a sulfonated derivative of polystyrene and a nucleoside analogue allows for a synergistic effect that is extremely important in vivo, allowing for an increase in the effectiveness of therapy of cat flu caused by FHV-1, especially infection caused by feline herpesvirus, lowering the doses of therapeutic agents used and reducing them possible toxicity and side effects. It also makes it possible to treat cat flu, especially infection caused by feline calicivirus or infection caused by feline herpesvirus resistant to currently available therapeutic agents used for this purpose.

The research has shown that a sulfonated polystyrene derivative, preferably PSSNa, does not act on the infected cell, but binds to a herpesvirus, such as preferably FHV-1, and thus blocks the spread of this virus, limiting the infection it causes. Thanks to this, such a derivative is extremely effective. In addition, it has very low toxicity and does not cause adverse effects.

The research also showed that the sulfonated derivative of polystyrene, preferably PSSNa, has a different mechanism of antiviral activity than the agents currently available on the market. Thanks to this, it can be effectively used in combination therapy with other antiviral drugs used in case of infection caused by feline herpesvirus, preferably with nucleoside analogues, especially acyclovir and/or penciclovir, in order to achieve a synergistic effect. This allows for increasing the effectiveness of therapy for infection caused by feline herpesvirus, reducing the doses of agents used and reducing toxicity while maintaining adequate therapeutic or prophylactic efficacy, as well as for effective treatment of the infection caused by resistant to currently available therapies mutants of feline herpesviruses.

Despite the fact that the adhesion factor for FCV is sialic acid [62], and not HS, whose mimetic is the polymer being studied, the inventors have shown that sodium salts of high molecular weight polystyrene sulfonate effectively inhibit FCV-induced infection in vitro caused by both F9 laboratory strain as well as six clinical strains K1, K2, K3, K5, K8, and K10. Inhibition is primarily seen in the late stages of infection, but antiviral activity is also seen in the early stages of infection.

The research also showed that the higher the molecular weight of the sodium polystyrene sulfonate used, the higher its activity against FCV. For example, a polymer with a molecular weight of 8 kDa has similar antiviral activity to polymers of polystyrene sulfonate with a lower molecular weight. In contrast, polystyrene sulfonate polymers with a molecular weight above 35 kDa exhibit significantly higher antiviral activity. The difference in activity is at least partly due to the fact that PSSNa with a higher molecular weight inhibits the infection process of FCV also in the early stages of infection—by inhibiting the adhesion of the virus to the cell surface.

The present invention will now be illustrated by means of embodiments and figures which are not, however, intended to limit the scope of protection of the invention in any way as defined in the patent claims.

SHORT DESCRIPTION OF FIGURES

FIG. 1 shows the results of a study on the effect of polymers of different molecular weights on the survival of Crandell-Rees feline kidney cells (CrFK). The results were presented for two selected concentrations, which were the highest concentration tested and the concentration at which high antiviral activity was demonstrated, respectively: 500 µg/ml (FIG. 1 A) and 20 µg/ml (FIG. 1 B). Values were normalized to 100% non-treated control cell survival.

Figure 2:
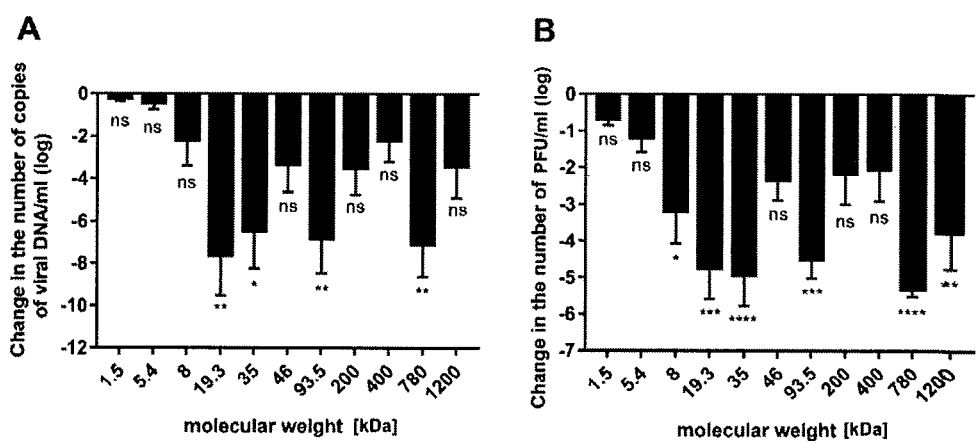

FIG. 2 shows the relationship between the molecular weight of a polymer and its activity against FHV-1 virus. Using real-time PCR, the number of viral DNA copies in 1 ml of medium was determined (FIG. 2 A), while plaque assays allowed to determine the number of infectious virions (FIG. 2 B). The replication test was carried out using polymers with different molecular weights at a concentration of 20 µg/ml. To determine the occurrence of statistically significant differences between the compared groups and the untreated control, a one-way ANOVA variance analysis supported by the Tukey's post-hoc test was performed. Values that were statistically significantly different from the viral control were marked with *, p<0.001; , p<0.01; *, p<0.05, while values that were not statistically different were marked as "ns". Results are presented as mean±SEM.

Figure 3:
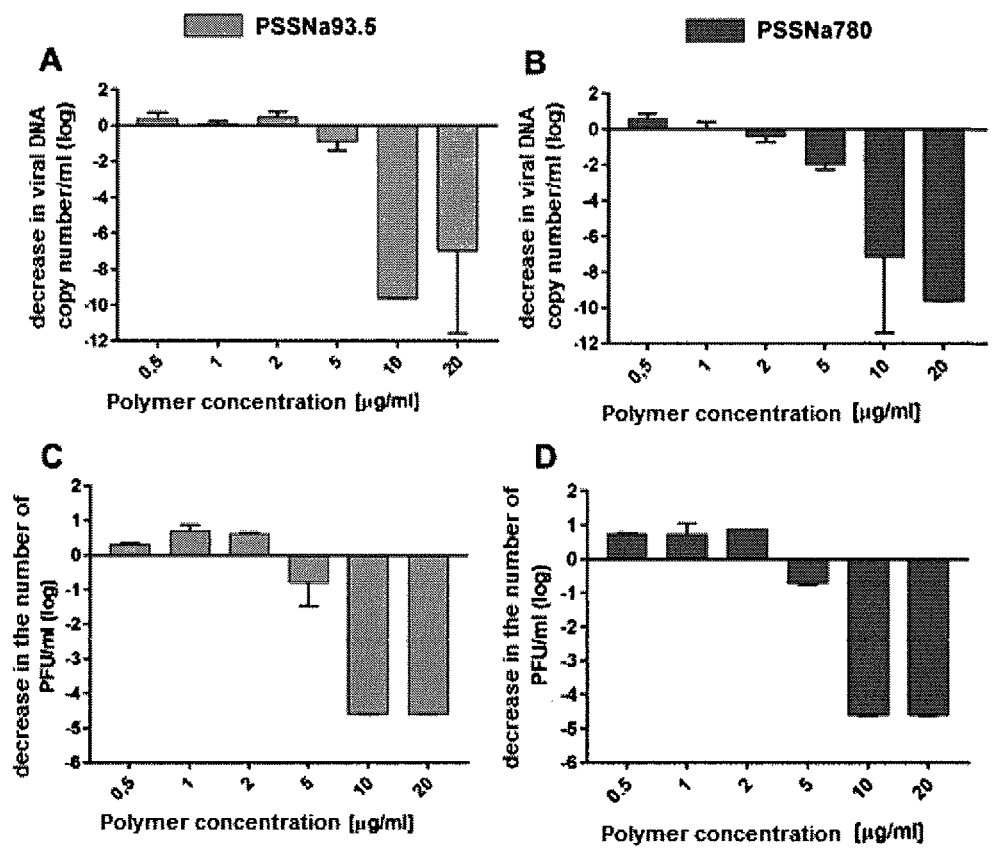

FIG. 3 shows the relationship between polymer concentration and its activity against FHV-1 virus. Using real-time PCR, the number of viral DNA copies in 1 ml of medium was determined (FIG. 3 A, FIG. 3 B), while plaque assays allowed to determine the number of infectious virions (FIG. 3 C, FIG. 3 D). The replication test was carried out using different concentrations of a polymer with a molecular weight of 93.5 kDa (FIG. 3 A, FIG. 3 C) and a polymer with a molecular weight of 780 kDa (FIG. 3 B, FIG. 3 D). The values have been normalized to the viral control.

Figure 4:
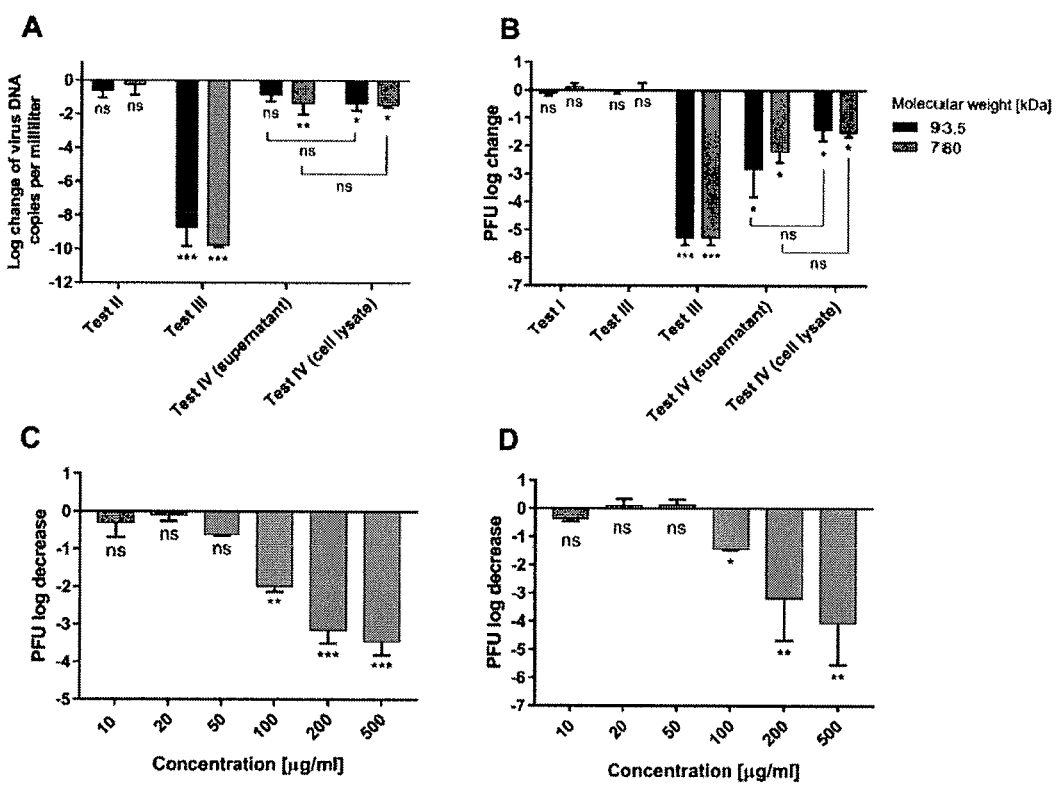

FIG. 4 shows the results of studies on the mechanism of action of PSSNa polymers. Four functional tests were performed to identify the stage at which the replication of FHV-1 virus by PSSNa polymer is inhibited. Using real-time PCR, the number of viral DNA copies in 1 ml of medium was determined (FIG. 4 A), while plaque assays allowed to determine the number of infectious virions (FIG. 4 B). Test I was carried out using different concentrations of a polymer with a molecular weight of 93.5 kDa (FIG. 4 C) and a polymer with a molecular weight of 780 kDa (FIG. 4 D). To determine the occurrence of statistically significant differences between the compared groups and the untreated polymer control, a one-way ANOVA variance analysis supported by the Tukey's post-hoc test was performed. Values that were statistically significantly different from the viral control were marked with *, $p<0.001$; , $p<0.01$; *, $p<0.05$, while values that were not statistically different were marked as "ns". Results are presented as mean±SEM.

Figure 5:
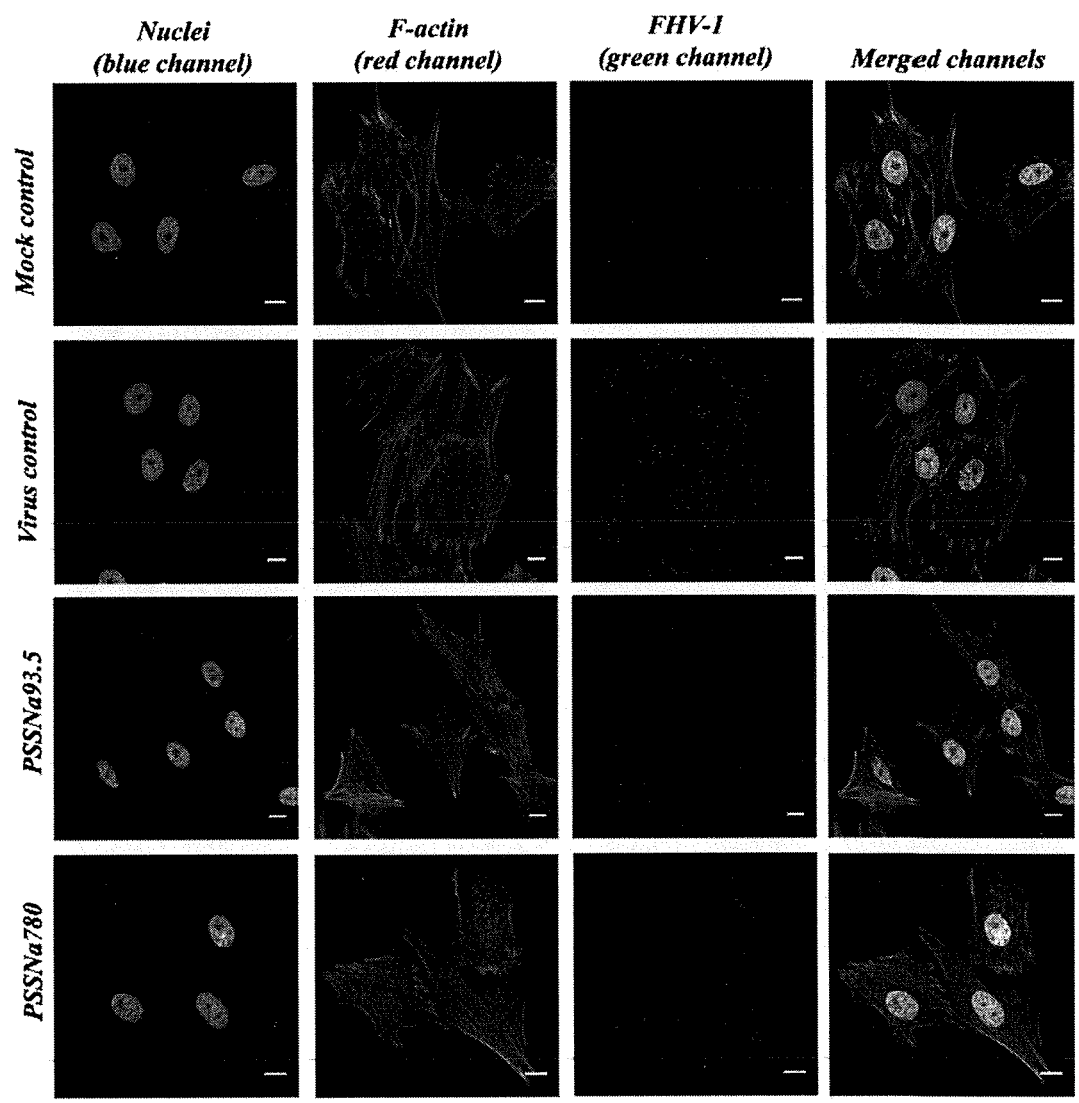

FIG. 5 shows the visualization of inhibition of FHV-1 virus infection of CrFK cells by PSSNa polymers. Individual channels and a combination of 3 channels are shown separately. The blue channel presents cell nuclei, the red channel is F-actin, while the green channel is FHV-1 virions. The figure shows visualizations of control cells (blank), viral control, cells treated with 93.5 kDa PSSNa and cells treated with 780 kDa PSSNa. The scale bar marks 10 µm.

Figure 6:
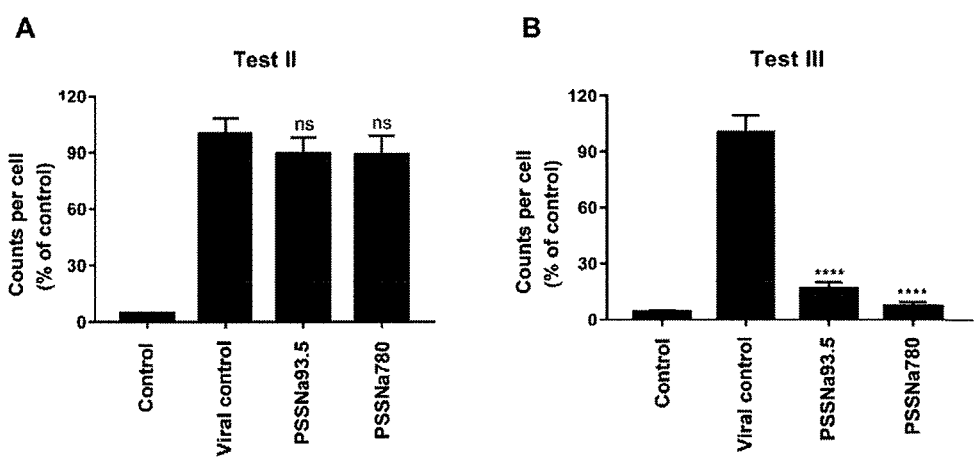

FIG. 6 shows the quantitative analysis of images obtained on a confocal microscope after conducting test II (FIG. 6A) and test III (FIG. 6B) made in ImageJ Fiji. The amount of virus per cell is presented as counts per cell (% of mean obtained for viral control). Results are presented as mean±SEM; data were from analysis of 10 different cells; the images were from three independent experiments. In order to determine the occurrence of statistically significant differences between the compared groups, a one-way ANOVA variance analysis was performed, supported by the Tukey post-hoc test. Values that were statistically significantly different from the viral control were marked with ****, $p<0.0001$, while values that were not statistically different were marked as "ns". Results are presented as mean±SEM.

Figure 7:
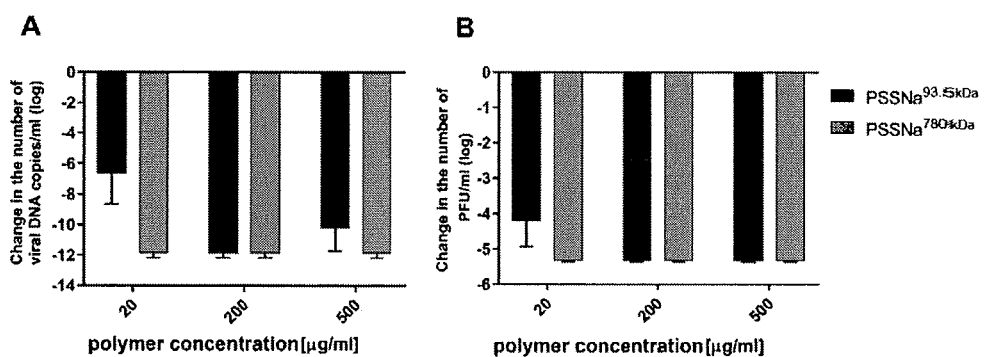

FIG. 7 shows the relationship between polymer concentration and its activity against the FHV-1 K7 clinical strain. A logarithmic change in the number of viral DNA per 1 ml of culture medium (FIG. 7A) was determined by real-time PCR, while plaque assays allowed to determine the logarithmic change in the number of infectious virions (PFU/ml) (FIG. 7B). The test was carried out using PSSNa polymers with two different molecular weights (93.5 kDa and 780 kDa) at three different concentrations (20, 200 and 500 µg/ml). The values were normalized to the viral control, i.e. infected cells not incubated with the polymer. Results are presented as mean±SEM.

Figure 8:
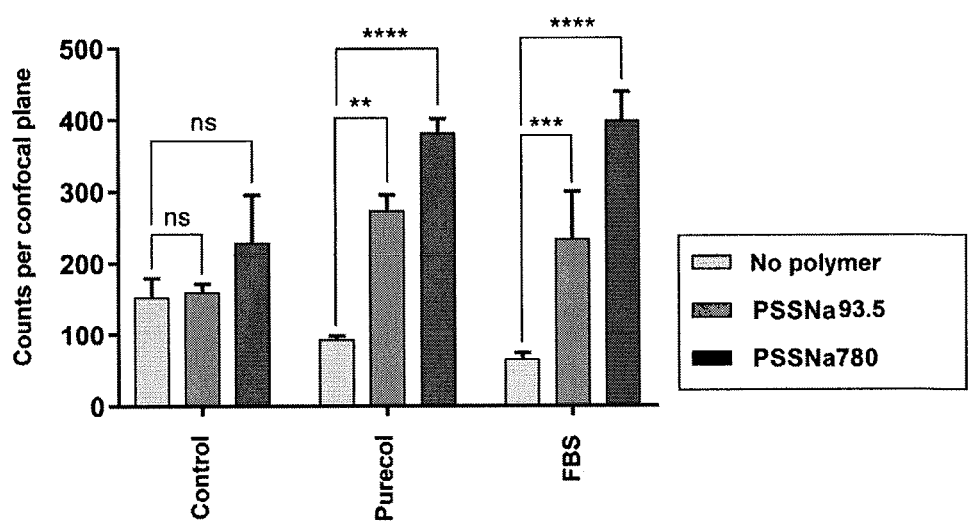

FIG. 8 shows the analysis of the ability of PSSNa polymers to bind to FHV-1 virus, which was presented as the number of counts (virions) per confocal plane. Counts were registered from 12 planes for each sample. Due to the fact that the given data did not meet the requirements for using the parametric test, the non-parametric Kruskal-Wallis test supported by Dunn's post-hoc test was carried out. Values that were statistically significantly different from the viral control were marked with **, $p<0.0001$; *, $p<0.001$; **, $p<0.01$; while values that were not statistically different were marked as "ns". The results were presented as median interquartile range.

Figure 9:
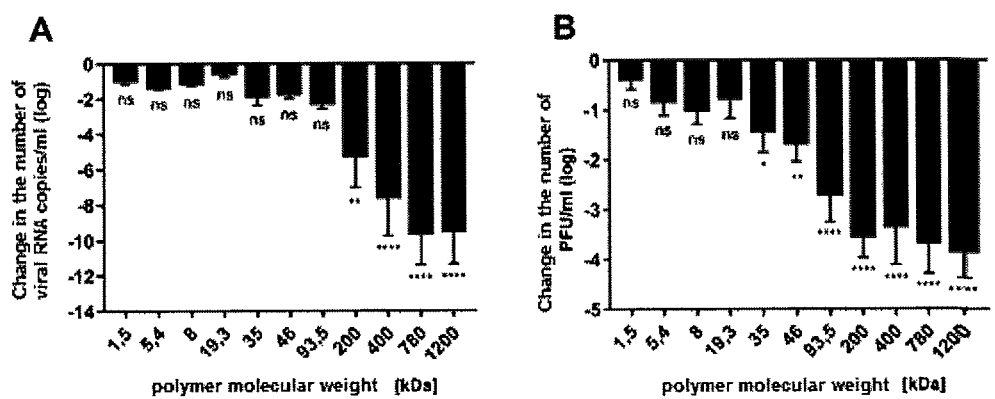

FIG. 9 shows the relationship between the molecular weight of a polymer and its anti-FCV activity. Using real-time RT-qPCR reactions, the number of viral RNA copies in 1 ml of medium was determined (FIG. 9 A), while plaque assays allowed to determine the number of infectious virions (FIG. 9 B). The test was carried out using polymers with different molecular weights at a concentration of 200 µg/ml. To determine the occurrence of statistically significant differences between the compared groups and the untreated polymer control, a one-way ANOVA variance analysis supported by Tukey's post-hoc test was performed. Values that were statistically significantly different from the viral control of each other were marked with **, $p<0.0001$; , $p<0.01$; *, $p<0.05$, while values that were not statistically different were marked as "ns". Results are presented as mean±SEM.

Figure 10:
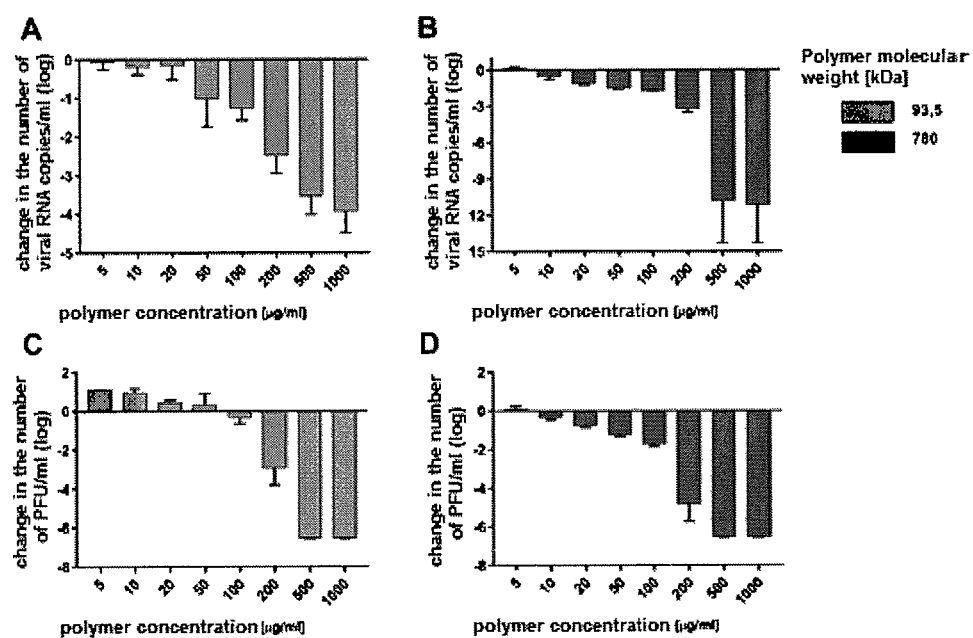

FIG. 10 shows the relationship between polymer concentration and its activity against FCV. Using real-time RT-qPCR reactions, the number of viral RNA copies in 1 ml of medium was determined (FIG. 10 A, FIG. 10 B), while plaque assays allowed to determine the number of infectious virions (FIG. 10 C, FIG. 10 D). The test was carried out using different concentrations of a polymer with a molecular weight of 93.5 kDa (FIG. 10 A, FIG. 10 C) and a polymer with a molecular weight of 780 kDa (FIG. 10 B, FIG. 10 D). The values have been normalized to the viral control.

Figure 11:
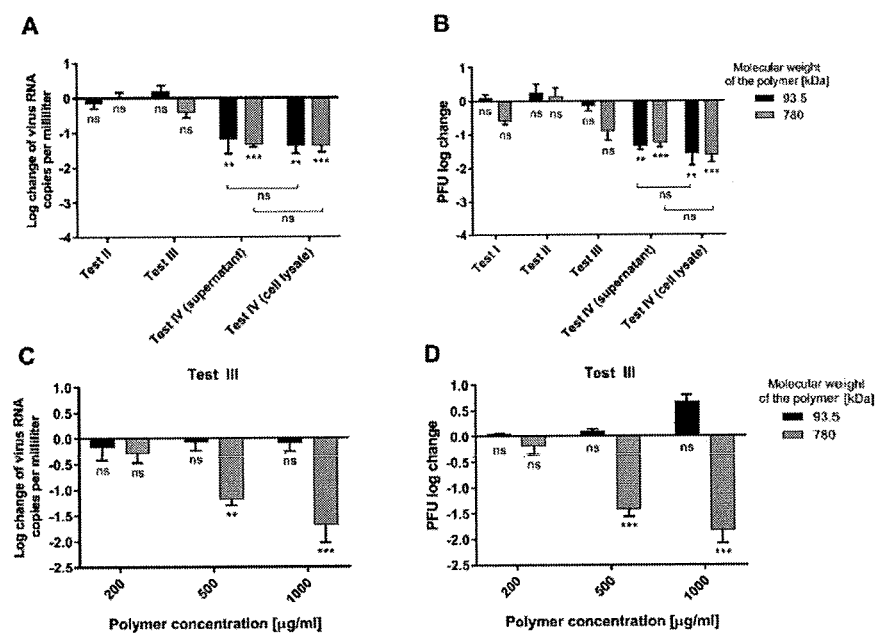

FIG. 11 shows the results of studies on the mechanism of action of PSSNa polymers. To identify the stage at which FCV infection is inhibited by the PSSNa polymer, 4 functional tests were carried out, described below, using a polymer with a concentration of 200 µg/ml. Using real-time RT-qPCR reactions, the number of viral RNA copies in 1 ml of medium was determined (FIG. 11 A), whereas plaque assays allowed to determine the number of infectious virions (FIG. 11 B). Test III was carried out using different concentrations of the polymer with a molecular weight of 93.5 kDa (FIG. 11 C) and a polymer with a molecular mass of 780 kDa (FIG. 11 D). To determine the occurrence of statistically significant differences between the compared groups and the untreated polymer control, a one-way ANOVA variance analysis supported by Tukey's post-hoc test was performed. Values that were statistically significantly different from the viral control were marked with *, $p<0.001$; , $p<0.01$, while values that were not statistically different were marked as "ns". Results are presented as mean±SEM.

Figure 12:
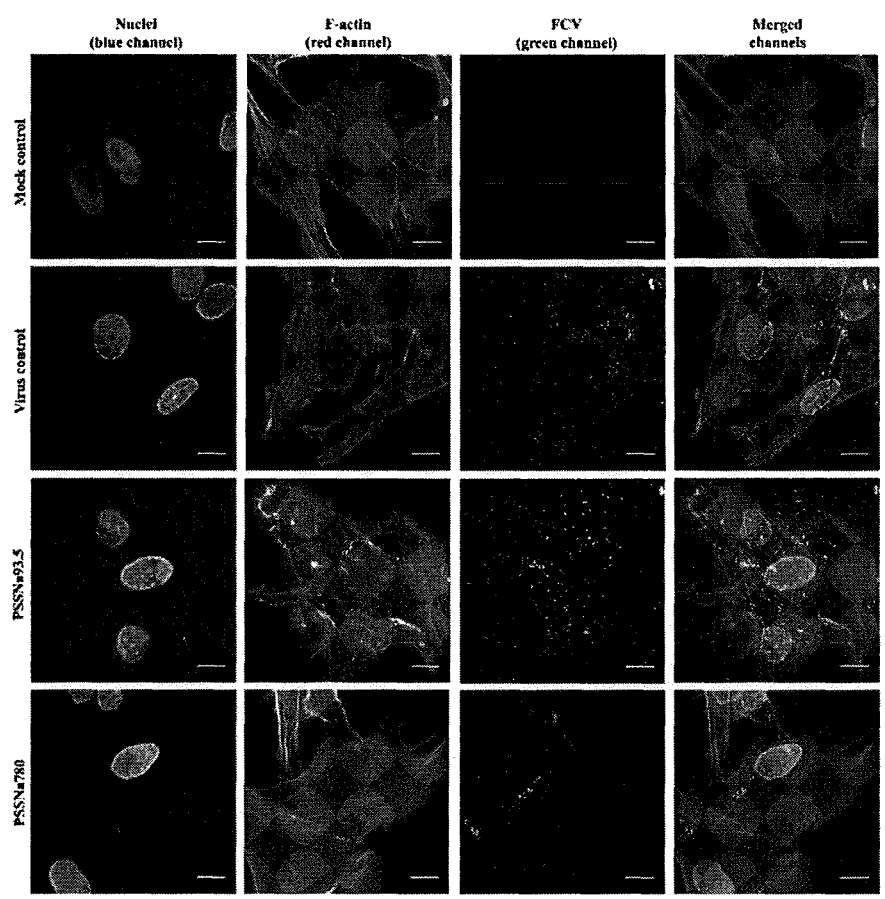

FIG. 12 shows a visualization of the inhibition of FCV infection of CrFK cells by PSSNa polymers at a concentration of 1000 µg/ml. Individual channels and a combination of 3 channels are shown separately. The blue channel presents cell nuclei, the red channel is F-actin, while the green channel is FCV virions. The figure shows visualizations of control cells, viral control, cells treated with PSSNa with a molecular weight of 93.5 kDa and cells treated with PSSNa with a molecular weight of 780 kDa. The scale bar marks 10 µm.

Figure 13:
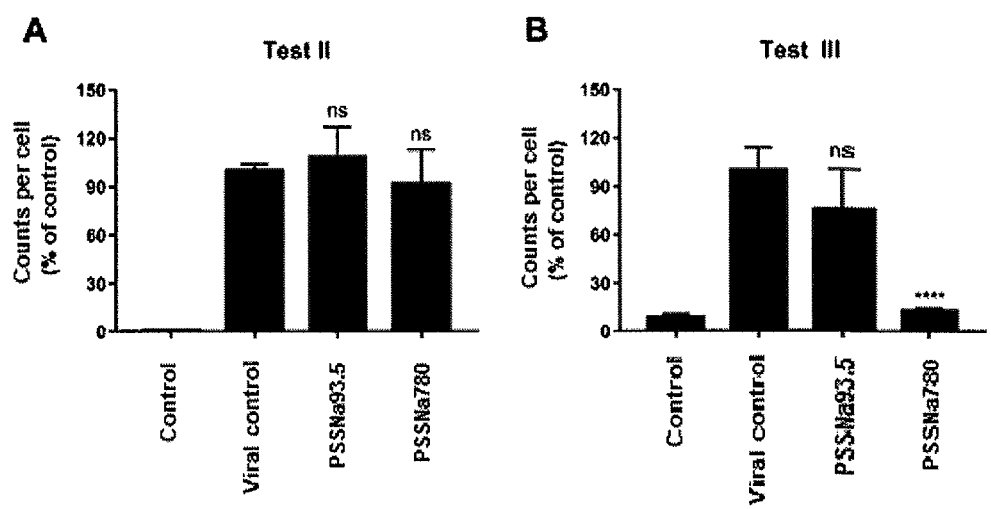

FIG. 13 shows the quantitative analysis of images obtained on a confocal microscope after conducting test II (A) and test III (B) made in ImageJ Fiji. The amount of virus per cell is presented as counts per cell (% of mean obtained for viral control). Results are presented as mean±SEM; data were from analysis of 10 different cells; the images were from three independent experiments. In order to determine the occurrence of statistically significant differences between the compared groups, a one-way ANOVA variance analysis supported by the Tukey post-hoc test was performed. Values that were statistically significantly different from the viral control were marked with ****, $p<0.0001$, while values that were not statistically different were marked as "ns".

Figure 14:
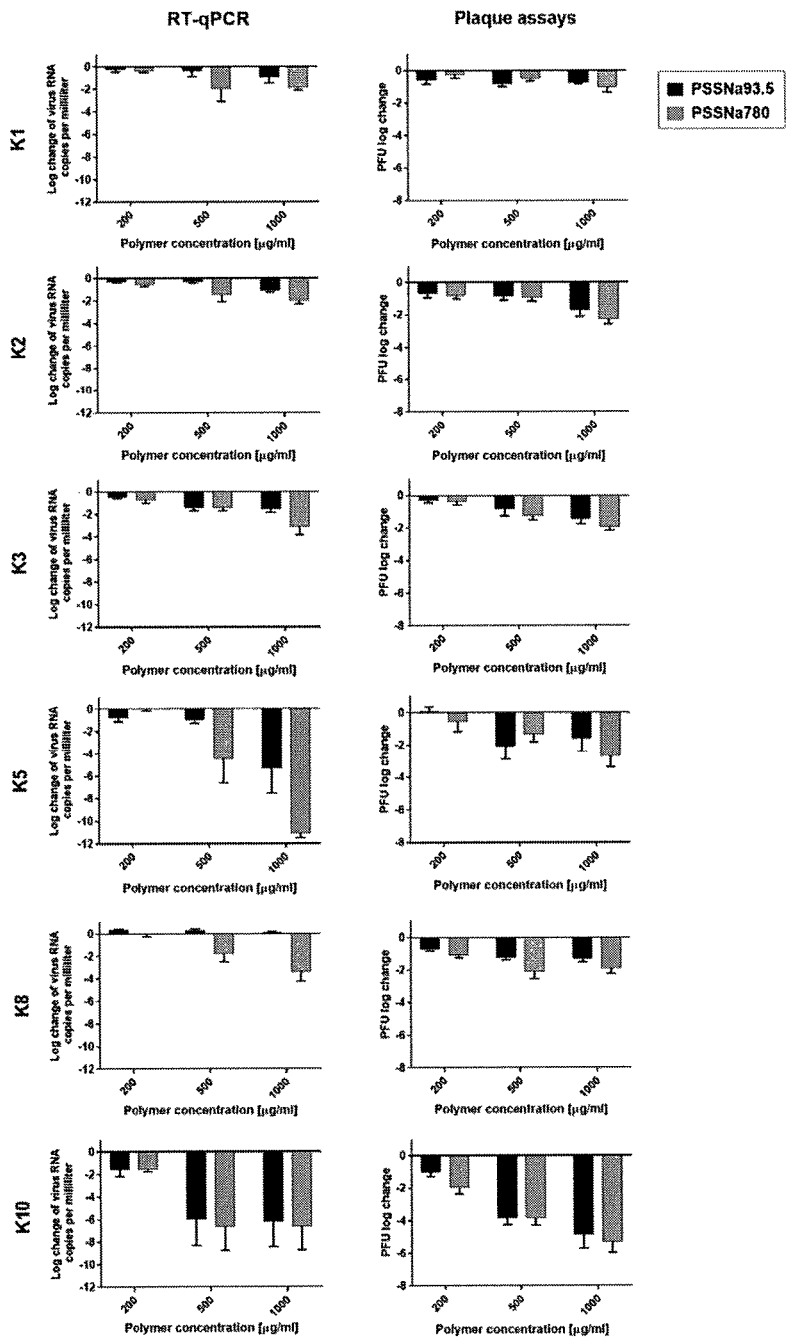

FIG. 14 shows the relationship between polymer concentration and its activity against FCV clinical strains. Using real-time RT-qPCR reactions, viral RNA number per 1 ml of culture medium was determined, while plaque assays allowed to determine the number of infectious virions. The test was carried out using polymers with two different molecular weights (93.5 kDa and 780 kDa) at three different concentrations (200, 500 and 1000 µg/ml). The values were normalized to the viral control, i.e. infected cells not incubated with the polymer. Results are presented as mean±SEM.

Figure 15:
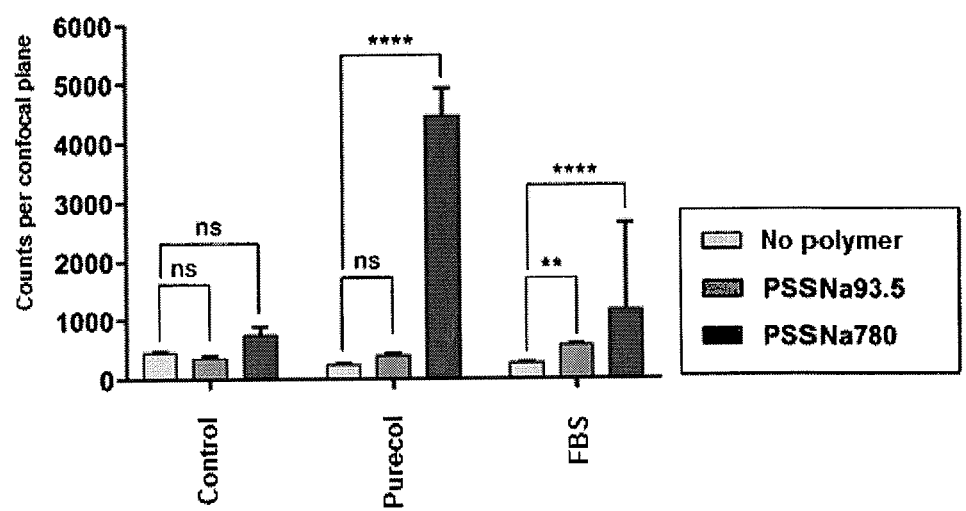

FIG. 15 shows an analysis of the ability of the PSSNa polymers to bind to virus, presented as the number of counts (virions) per confocal plane. Counts were made from 12 planes for each sample. Due to the fact that the given data did not meet the requirements for using the parametric test, the non-parametric Kruskal-Wallis test supported by Dunn's post-hoc test was carried out. Values that were statistically significantly different from the viral control were marked with **, $p<0.0001$, , $p<0.01$, while values that were not statistically different were marked as "ns". The results were presented as median±interquartile range.

Figure 16:
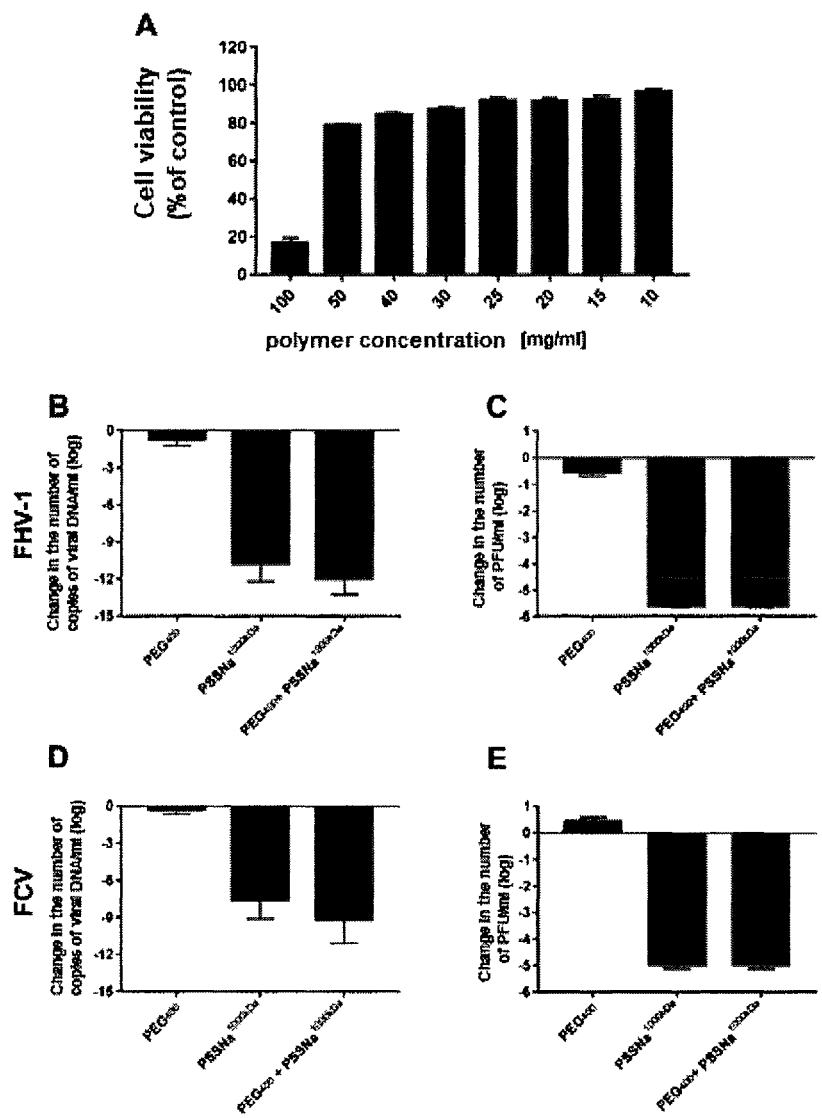

FIG. 16 shows in vitro analysis of the antiviral activity of the PSSNa-PEG hydrogel. The cytotoxicity of PEG400 at concentrations of 100, 50, 40, 30, 25, 20, 15 and 10 mg/ml was determined by the XTT test (A). The results were normalized to control cells (untreated with polymer), which was 100%. The viral replication assay was performed using CrFK cells in the presence of PEG400 (30 mg/ml) and PSSNa1000 kDa (200 µg/ml) for FHV-1 (B, C) and for FCV (D, E). Inhibition of viral infection was determined by real-time PCR and presented as a logarithmic change in the number of copies of DNA (for FHV-1) or RNA (for FCV) per milliliter (B, D) or using a plaque assay and presented as the logarithmic change in the number of PFU/ml (C, E). The results were normalized to viral control, i.e. infected cells untreated with polymer, and presented as mean±SEM from three independent experiments.

EXAMPLES

All the tests and experimental procedures described below were carried out using commercially available test kits, reagents and apparatus, following the recommendations of the manufacturers of the kits, reagents and apparatus used, unless expressly stated otherwise. The test parameters indicated above were measured using standard, commonly known methods used in the field to which the present invention belongs.

Example 1

The effect of sodium polystyrene sulfonate (PSSNa) of different molecular weight on the survival of CrFK cells The cytotoxicity of polymers was determined using the XTT Viability Assay Kit (Biological Industries, Israel), which quantifies the ability of metabolically active cells to transform a substrate into its colored derivative. Permissive CrFK cell line (Crandell-Rees cat kidney cortex, Felis catus, Crandell-Rees Feline Kidney Cells, ATCC® CCL-94™) was used to conduct the experiment. Test conditions were standard. The cells were cultured for 48 hrs in DMEM (Dulbecco's Modified Eagle's Medium) medium supplemented with 3% FBS (heat inactivated fetal bovine serum), penicillin, streptomycin, gentamicin and PSSNa polymers with different molecular weights. FIG. 1 shows the results for two selected polymer concentrations: 500 µg/ml (FIG. 1 A, highest concentration tested) and 20 µg/ml (FIG. 1 B, concentration at which high antiviral activity was demonstrated). Briefly, after culturing CrFK cells in a 96-well plate for 24 hrs, old medium was removed and 100 µl of fresh medium containing the selected polymer concentration was added to each well of the plate. The control sample did not contain polymer in the medium. The polymer medium was then removed and 100 µl of fresh medium with 20 µl of activated 2,3-bis-(2-methoxy-4-nitro-5-sulfenyl)-(2H)-tetrazoline carboxyanilide (XTT) was added to each well. After 2 hrs incubation, the supernatant was transferred to a transparent 96-well plate and absorbance at 480 nm was measured in a standard manner using a spectrophotometer. The obtained results values were normalized to the absorbance measured for control cells (without polymers), which were assigned 100% survival value. Eleven PSSNa polymers with different molecular weights were tested (1.5; 5.4; 8; 19.3; 35; 46; 93.5; 200; 400; 780 and 1200 kDa).

The obtained results indicate the lack of significant cytotoxicity of the polymers in the tested molecular weight range and in the tested concentration range, i.e. from 20 µg/ml to 500 µg/ml.

Example 2

The effect of sodium polystyrene sulfonate (PSSNa) on the replication of feline herpesvirus type 1 (FHV-1)

To determine the activity of sodium polystyrene sulfonate (PSSNa) against feline herpesvirus type 1 (strain C-27, ATCC: VR-636), a test of the effect of this polymer on viral replication was performed. In this experiment, the polymer was present at every stage of viral replication—before, during and after infection. Briefly, completely confluent CrFK cells were seeded 24 hrs prior to the experiment in a 96-well plate. Then the medium was discarded and 20 µl of fresh medium containing polymer was added. Plates were incubated for 30 min at 37° C., then the medium with the polymer was discarded and 50 µl of polymer solution in 3% DMEM or 3% DMEM without polymer (control sample) added with blank or FHV-1 virus (strain C-27) with $TCID_{50}$ titer (50% of tissue culture infective dose)=400/ml. Plates were incubated for 2 hrs at 37° C., then cells were washed twice with 1×PBS to remove unbound viral particles. Finally, 100 µl of polymer solution in 3% DMEM was added to each well and the cells were incubated for 48 hrs. After this time, the supernatant was collected to quantify infection using (a) quantitative PCR (qPCR) and (b) plaque assay as follows:

(a) qPCR

Isolation of viral DNA was carried out 48 hrs after infection using the Viral DNA/RNA Isolation Kit (A&A Biotechnology, Poland) isolation test according to the protocol provided by the manufacturer. The DNA thus isolated was the template for performing real-time quantitative PCR (qPCR). Primers known in the art to amplify a conserved fragment of the gene sequence for glycoprotein B and a probe complementary to this fragment were used [43]. The primer and probe sequences used are shown in Table 1.

TABLE 1

Sequences of primers and probe used for real-time PCR

| Oligonucleotide | Oligonucleotide sequence 5'→3' |
|---|---|
| Forward primer | AGAGGCTAACGGACCATCGA (SEQ ID NO: 1) |
| Reverse primer | GCCCGTGGTGGCTCTAAAC (SEQ ID NO: 2) |
| Probe | TATATGTGTCCACCACCTTCAGGATCTACTGTCGT (SEQ ID NO: 3) |

Briefly, the qPCR reaction was carried out as follows. 2.5 µl of isolated viral DNA was amplified in a 10 µl reaction containing 1×Kapa Probe Fast qPCR MasterMix mixture (Sigma-Aldrich, Poland), 100 nM specific probe labeled with 6-carboxyfluorescein (FAM) and 6-carboxytetramethylrhodamine (TAMRA) (5'-FAM-TAT ATG TGT CCA CCA CCT TCA GGA TCT ACT GTC GT-TAMRA -3' (SEQ ID NO:3)), and 450 nM of each starter (5'-AGA GGC TAA CGG ACC ATC GA-3' (SEQ ID NO:1) and 5'-GCC CGT GGT GGC TCT AAA C-3' (SEQ ID NO:2)). The above-mentioned specific probe and primers amplified a 81 bp fragment of sequence from the FHV-1 glycoprotein B (gB) gene to measure the number of viral DNA copies in the sample [43]. The reaction was performed in a thermocycler (CFX96 Touch™ Real-197 Time PCR Detection System, Bio-Rad) under the following conditions: 3 min at 95° C., then 39 cycles of 15 seconds at 95° C. and 30 seconds at 58° C.

Appropriate standards were prepared to evaluate the copy number of viral DNA in the sample. The gB sequence fragment was amplified using the primers described above. The DNA thus obtained was cloned into the pTZ57R/T plasmid (Thermo Scientific, Poland) using the InsTAclone PCR Cloning Kit (Thermo Scientific, Poland). Transformation of *E. coli* TOP10 strain (Life Technologies, Poland) and propagation of the plasmid vector in a standard manner was performed. The plasmid was then purified using the GeneJET Plasmid Miniprep Kit (Thermo Scientific, Poland) and subjected to linearization by digestion with KpnI restriction enzyme. The concentration of linearized DNA was assessed by spectrophotometric measurement and the number of DNA copies in 1 ml of medium was calculated. Eight consecutive 10-fold serial dilutions were used as the template for real-time PCR. The ability of polymers to inhibit FHV-1 virus replication was determined as a decrease in the number of viral DNA copies in 1 ml of medium.

b) Plaque Assays

Quantitative analysis of infectious FHV-1 virions was performed on CrFK cells that were plated in 24-well plates. 80-90% confluent cells were infected 24 hrs from plating by adding fresh, 10-fold serial dilutions of supernatants, after which the cells were incubated for 1 hour at 37° C. in an atmosphere containing 5% $CO_2$. Then the cells were washed once with 1×PBS to remove unbound viral particles and 0.5 ml DMEM medium supplemented with 10% heat inactivated fetal bovine serum (FBS, Life Technologies, Poland), penicillin (100 U/ml), streptomycin (100 µg/ml) and 1% methylcellulose (Sigma-Aldrich, Poland) was applied. The time it takes for plaques to form by FHV-1 virus is about 72 hrs. After this time, the cells were fixed and stained with 0.1% crystal violet solution dissolved in 50% (v/v) methanol:water. Plaques were counted and the values obtained were plotted as PFU (plaque forming unit) per ml of medium.

In this way, the relationship between the molecular weight of the polymer and its activity against the FHV-1 virus was investigated. The number of viral DNA copies in 1 ml of medium was determined by quantitative real-time PCR, while plaque assays allowed to determine the number of infectious virions. As shown in FIG. 2, the replication test was carried out using polymers with different molecular weights and a concentration of 20 µg/ml. The obtained value results were normalized and presented as a logarithmic change relative to the viral control.

The conducted research have shown that the polymers tested have antiviral activity and inhibit the replication of FHV-1 virus. There was no correlation between antiviral activity and polymer molecular weight. However, it was observed that polymers with a molecular weight above 8 kDa showed the best antiviral activity. Polymers with a molecular weight below 8 kDa showed weaker antiviral activity.

Example 3

Relationship between antiviral activity of sodium polystyrene sulfonate (PSSNa) and its concentration in the medium To determine the $IC_{50}$ (50% inhibitory concentration, 50% inhibition of viral replication) of the sodium polystyrene sulfonate (PSSNa), the effect of different concentrations of this polymer on viral replication was tested. This test was carried out analogously to Example 2. The relationship between polymer concentration and its activity against FHV-1 virus was investigated.

Briefly, the number of viral DNA copies in 1 ml of medium was determined by real-time PCR (FIG. 3 A, FIG. 3 B), while plaque tests allowed to determine the number of infectious virions (FIG. 3 C, FIG. 3 D). The replication test was carried out using different concentrations of the polymer with a molecular weight of 93.5 kDa (FIG. 3 A, FIG. 3 C) and a molecular weight of 780 kDa (FIG. 3 B, FIG. 3 D). The values have been normalized to the viral control.

The calculated $IC_{50}$ values are shown in Table 2 below.

TABLE 2

IC50 values for polymers determined by real-time PCR and plaque assay

| | $IC_{50}$ ± SD [µg/ml] | |
|---|---|---|
| Polymer | qPCR | Plaque assay |
| PSSNa93.5 | 2.25 ± 1.01 | 5.74 ± 1.32 |
| PSSNa780 | 2.28 ± 1.01 | 5.06 ± 1.33 |

The tested polymers have been shown to inhibit the replication of FHV-1 virus, in particular at low, non-toxic concentrations.

Example 4

Determination of mechanism of the antiviral action of PSSNa polymers

The mechanism of action of PSSNa polymers was studied as follows. In order to identify the stage at which FHV-1 virus replication is inhibited by the PSSNa polymer, the 4 functional tests described below were performed.

Test I (Inactivation Test)

The concentrated virus suspension was incubated with the polymer for 1 hour at 22° C. with shaking, and then the samples were diluted to reduce the polymer concentration below the range of concentrations in which it was active, and the viral titer was assessed using a plaque assay.

This test allows to determine whether inhibition occurs through the interaction between the polymer and the virus, which prevents the infection of cells. In other words it can determine whether the test compound has a direct effect on the virus.

Test II (Cell Protection Test)

The cells seeded 24 hrs prior the experiment were incubated in the presence or absence of polymer for 1 hour at 37° C. The plates were then washed twice with 1×PBS to remove unbound polymer particles, after which fresh medium with mock sample or the virus (400 $TCID_{50}$/ml) was added to each well in equal volume and incubated for 2 hrs at 37° C.

The plates were then washed twice with 1×PBS to remove unbound viral particles, fresh medium was applied to the cells and incubated for 48 hrs at 37° C. Finally, supernatants were collected and virus replication was quantified using plaque assay and qPCR.

This test determines whether the polymer by e.g. binding to cell surfaces is able to "protect" them from infection by preventing interaction with the entry receptor.

Test III (Adhesion Test)

This test was carried out at 4° C. at which intracellular transport is inhibited. Briefly, confluent CrFK cells were cooled at 4° C. for 20 min. Then cold fresh medium with or without virus (400 $TCID_{50}$/ml) and with or without polymer was applied to the cells. Plates were incubated for 1 hour at 4° C. Intracellular transport at this temperature was stopped, but adsorption of viruses to cellular receptors was possible. After incubation, the cells were washed twice with ice-cold 1×PBS to remove unbound viral particles and unbound polymer, fresh medium was added and the cells were incubated for 48 hrs at 37° C. After 48 hrs supernatant was collected and virus was quantified using qPCR and plaque assay.

This test allows to determine whether inhibition occurs through the competition of the polymer with the virus for the adhesive agent and/or whether the polymer, interacting with the adhesive agent, prevents its interaction with the virus.

Test IV (Late Stages Test: Replication, Assembly and Release)

In this test, infection was first carried out by incubating the cells with the virus, then, after incubation, unbound virions were washed away with PBS solution and the polymer was applied. Briefly, fresh medium containing a non-infectious mock sample or a virus sample (400 $TCID_{50}$/ml) in equal volume was applied to confluent CrFK cells, then plates were incubated for 2 hrs at 37° C. After incubation, the wells were washed twice with 1×PBS to remove unbound viral particles, then fresh medium containing the selected polymer concentration was added to each well. Plates were incubated for 48 hrs at 37° C. After 48 hrs supernatants were collected, then separately PBS was added to the wells and cells were subjected to two freeze-thaw cycles to obtain cell lysates, virus replication was quantified using plaque assay and qPCR.

This test shows whether inhibition of the virus replication occurs at late stages of infection, e.g. replication, assembly, release. Whereas a separate determination of viral titer in supernatants and cell lysates allows to determine whether inhibition occurs at the stage of viral replication or at the stage of release of infectious virions.

In the tests described above, the number of viral DNA copies in 1 ml of medium was determined by real-time PCR (FIG. 4 A), whereas plaque assays allowed to determine the number of virions (FIG. 4 B). Test I was carried out using different concentrations of 93.5 kDa PSSNa (FIG. 4 C) and 780 kDa PSSNa (FIG. 4 D).

The conducted research showed that the polymer interacts directly with the virus, which prevents the virus from entering the CrFK cell. It has also been shown that the higher the polymer concentration, the greater its effectiveness in binding FHV-1. Very strong inhibition of infection is also visible at the adhesion stage, but it is worth noting that during this test the polymer and the virus are at the same time in the culture medium, which allows the polymer to bind to the virus and inhibit its ability to internalize. Antiviral activity is also visible in the late stages of infection, which is related to the interaction of progeny virions with the polymer present in the medium, the possibility of a second, independent mechanism of action was excluded by additional experiments.

Example 5

Visualization of inhibition of eeplication of feline herpesvirus type 1 by two Selected PSSNa polymers by confocal microscopy To prepare slides, CrFK cells were plated in a standard manner onto microscope slides 24 hrs prior to the experiment. The cells were then cooled and incubated for one hour at 4° C. in a standard manner in the presence of virus or virus and polymer. After a given incubation time, the unbound viral particles were washed away, the preparations were fixed and stained in a standard manner. For immunofluorescence staining, mouse anti-FHV-1 primary antibodies and goat anti-mouse secondary antibodies conjugated to the fluorescent dye Alexa Fluor 488 were used to visualize virions, phalloidin conjugated to Alexa Fluor 647 to stain F-actin filaments and 4',6'-diamidine-2-phenylindole (DAPI) for staining nuclear DNA. Maximum projections were presented.

FIG. 5 shows the visualization of inhibition of FHV-1 virus infection of CrFK cells by PSSNa polymers. The signal for each of the colors is presented separately (blue, red and green channels) and the combination of the signals from all three dyes (combined channels). Cell nuclei are shown in blue, F-actin in red, and FHV-1 virions in green. The figure shows visualizations of control cells (mock sample), viral control, cells treated with 93.5 kDa PSSNa and cells treated with 780 kDa PSSNa. The scale bar corresponds to 10 μm.

Microscopic visualizations show a significant decrease in the number of FHV-1 virions on CrFK cells in the presence of the PSSNa polymers tested. The study confirms the efficacy of the sulfonated polystyrene derivative against infection caused by feline herpesvirus.

Example 6

Assessment of the synergistic effect of sulfonated polystyrene derivatives and nucleoside analogues The synergistic effect of a representative sulfonated polystyrene derivative, PSSNa, and exemplary nucleoside analogues with a different mechanism of antiviral activity, i.e. acyclovir (ACV) and penciclovir (PCV), have been studied in a known manner [44], with some modifications. The experiment was carried out in two systems. One system used a constant concentration of PSSNa (compound II) and different concentrations of the corresponding test nucleoside analogue (compound I), while the other system used a constant concentration of the corresponding test nucleoside analogue (compound II) and different concentrations of PSSNa (compound I). Briefly, the XTT test was first performed as described above to exclude drug-associated toxicity, then the virus replication test was performed as described above to determine the $IC_{50}$ value for FHV-1 strain C-27 at 400 $TCID_{50}$/ml for ACV and PCV (using qPCR). Then, two types of serial dilutions were prepared to assess the synergistic effect of ACV/PCV and a PSSNa polymer with a molecular weight of 780 kDa (PSSNa780): (1) six 2-fold serial dilutions of compound I starting from a concentration equal to $IC_{50}$ of compound I mixed with compound II at a concentration of equal to $IC_{50}$ of compound II; (2) six 2-fold serial dilutions of compound II starting at a concentration equal to $IC_{50}$ of compound II were mixed with compound I at a concentration equal to $IC_{50}$ of compound I. The maximum concentrations of both compounds were therefore equal to half of their $IC_{50}$. As previously described, the virus replication assay was carried out on completely confluent CrFK cells. After 48 hours supernatants were collected and the number of virions was assessed using a quantitative qPCR reaction in a standard manner.

The synergistic effect was evaluated by calculating the combination index (CI) according to the formula:

$$CI = \frac{d_1}{D_1} + \frac{d_2}{D_2} \quad (1)$$

wherein:

$d_1$ is the concentration of compound I in the presence of $IC_{50}/2$ of compound II causing a 50% decrease in virion number;

$d_2$ is the concentration of compound II in the presence of $IC_{50}/2$ of compound I causing a 50% decrease in virion number;

$D_1$ is the $IC_{50}$ of compound I;

$D_2$ is the $IC_{50}$ of compound II.

The CI indicates the synergistic effect of the drugs: CI>1 means an antagonistic effect, CI about 1 means an additive effect, and CI<1 means a synergistic effect.

The conducted research showed that two nucleoside analogues, which have different mechanisms of action from the mechanism of action of PSSNa, i.e. acyclovir (ACV) and penciclovir (PCV), show a synergistic effect with the sodium salt of polystyrene sulfonate (PSSNa). The calculated CI values for these compounds were 0.92 for PSSNa780/ACV and 0.46 for PSSNa780/PCV. This synergistic effect is particularly relevant in in vivo clinical settings.

Example 7

Quantitative analysis of inhibition of early stages of cell infection after incubation with or without PSSNa polymer having a molecular weight of 93.5 kDa and 780 kDa.

Representative microscope images shown in Example 5 were quantified in ImageJ Fiji and the number of FHV-1 C-27 virions per cell counted—both internalized and cell-adherent particles. The percentage analysis of the virus counts per cell is shown in FIG. 6. It was shown that after the cell protection test (test II), the number of FHV virions did not decrease in the presence of polymer, which is consistent with previously obtained results. It was also confirmed that after performing the adhesion test (test III) a statistically significant decrease in the amount of viruses per cell was visible compared to the viral control both after using the polymer with a molecular weight of 93.5 kDa and 780 kDa. The results for each of the systems are presented as mean counts of 10 CrFK cells. By quantitative analysis of microscopic images, polymers have been shown to inhibit infection in the early stages of infection. The obtained percentage analysis of virus counts per cell is consistent with microscopic observations.

Example 8

The effect of sodium polystyrene sulfonate (PSSNa) on infectivity of the FHV-1 K7 clinical strain The veterinary strain was obtained thanks to the kindness of veterinarians at the Homeless Animal Shelter in Krakow, who took swabs from cats showing symptoms of upper respiratory tract infection. Swabs were taken from the throat and nasal cavity using special swabs sticks for transporting viral clinical samples. To eliminate possible bacterial and fungal infection, the samples were filtered using sterile, disposable filters with a pore diameter of 0.2 which should not be a barrier to FHV virions. The filtered transport medium was transferred to a 12-well plate with confluent CrFK cells. Plates were incubated up to 96 hours, monitoring the wells twice a day. If the cytopathic effect (CPE) was visible, the supernatant was collected and subjected to plaque assays (procedure described in Example 10b). After 48 hrs, single, well-visible plaques were selected and agar pierced at this site with a sterile pipette tip. The tip was then transferred and the medium was touched with it on a new 12-well plate containing fully confluent CrFK cells. If a cytopathic effect occurred, the supernatant was transferred and aliquoted to new freezing tubes and stored at −80° C. The species affiliation of each strain was confirmed by sequence fragment sequencing for TK thymidine kinase. The origin of the FHV-1 K7 clinical strain is characterized in Table 3.

TABLE 3

Origin of the FHV clinical strain.

| Strain | Collection date | Cat's gender | Cat's age | Place of swab collection | Disease symptoms | The origin of the swab |
|---|---|---|---|---|---|---|
| FHV-1 K7 | Nov. 25, 2018 | ♂ | 1 year | Throat | Inflammation of the upper respiratory tract, sneezing, purulent discharge from the nose | Shelter for homeless animals in Krakow |

In order to determine the antiviral activity of sodium polystyrene sulfonate (PSSNa) against the isolated clinical strain FHV-1 K7, the effect of different concentrations of this polymer with two selected molecular weights (93.5 kDa and 780 kDa) on viral infection was tested. The viral replication test was carried out analogously to Example 2. Briefly, a logarithmic change in the number of viral DNA copies per ml from the isolated infectious material was determined by real-time quantitative PCR (FIG. 7A), while plaque assays allowed to determine the logarithmic change in the infectious number virions (FIG. 7B). The values were normalized to the viral control, i.e. infected cells not incubated with the polymer.

The tests confirmed that the polymers tested have antiviral activity also against the clinical strain FHV in low, non-toxic concentration. The polymer completely inhibited viral replication, both the viral DNA copy number and the number of infectious virions were below the detection threshold.

Example 9

Interaction test: analysis of the FHV-1 virus binding capacity to surfaces coated with PSSNa polymer, analysis of direct virus-polymer interaction.

The interaction test allows to determine if there is a direct interaction between the inhibitor and the virus. Sterile cover slips were placed inside a 12-well plate. To compensate for the negative charge of coverslips, they were incubated with 3% FBS or bovine collagen (Purecol) in PBS for 2 hrs at 37° C., slides incubated in PBS were the control. The slides were then washed twice with PBS, and incubated with PBS solution or polymer at a concentration of 20 μg/ml was added in an amount of 1 ml per well. Samples were incubated for 2 hrs at 37° C. This step is to cover the slides with a negatively charged polymer. Then, the unbound polymer particles were washed away with PBS solution. The next step was incubation of slides with a viral suspension of $TCID_{50}$ equal to 63,000,000/ml or control for 2 hrs at 37° C. It was assumed that if there is a direct interaction between the polymer and the virus, the virions will bind to the surface covered with the polymer. Unbound particles were washed away with PBS solution and the material was prepared for confocal microscopy imaging. Immunofluorescent staining was performed, preparations were visualized, and then the number of viral particles per confocal plane was counted in ImageJ Fiji. Quantitative analysis is shown in FIG. 8.

Example 10

Effect of polystyrene sulfonate sodium (PSSNa) on FCV infection

To determine the antiviral activity of sodium polystyrene sulfonate (PSSNa) against FCV (F-9, ATCC® VR-782™ strain), a test of the effect of compounds on viral infection was performed. In this experiment, the polymer was present at every stage of the viral infection. In the experiment, completely confluent CrFK cells were used after 24 hrs from plating on a 96-well plate. The medium was removed and 20 μl of fresh medium containing polymer was added. Plates were incubated for 30 min at 37° C., then the medium with the polymer was removed and 50 μl of polymer solution in 3% DMEM or 3% DMEM without polymer (control sample) were added, without virus (control sample) or with FCV titer 400 $TCID_{50}$ ml. Plates were incubated for 1.5 hrs at 37° C., then cells were washed twice with PBS solution to remove unbound viral particles. Finally, 100 μl of polymer solution in 3% DMEM was added to each well and the cells were incubated for 18 hrs. After this time, the supernatant was collected to assess the number of viruses using (a) quantitative RT-PCR (RT-qPCR) and (b) plaque assays, as follows:

a) Rt—qPCR

Isolation of viral RNA was carried out in a standard manner using a commercially available RNA isolation kit (Viral DNA/RNA Isolation Kit, A&A Biotechnology, Poland) according to the protocol provided by the manufacturer. The isolated RNA was reverse transcribed (RT) using a commercially available kit (High Capacity cDNA Reverse Transcription Kit, Life Technologies, Poland). The cDNA thus obtained was the template for performing quantitative real-time PCR (qPCR). Primers known in the art to amplify a conservative fragment of the FCV genome sequence and a probe complementary to this fragment were used [63]. The primer and probe sequences used are shown in Table 4.

TABLE 4

Sequences of primers and probe used for quantitative real-time PCR

| Oligonucleotide | Oligonucleotide sequence 5'→3' |
|---|---|
| Sense primer | CAACCTGCGCTAACG (SEQ ID NO: 4) |
| Antisense primer | TCCCAY*ACAGTTCCAAATT (SEQ ID NO: 5) |
| Probe | CTTAAATAY*TATGATTGGGAY*CCCCA (SEQ ID NO: 6) |

Y* - degenerate nucleotide (C or T)

Briefly, the qPCR reaction was carried out as follows. 2.5 μl of isolated viral DNA was amplified in a 10 μl reaction containing 1×Kapa Probe Fast qPCR MasterMix mixture (Sigma-Aldrich, Poland), 100 nM specific probe labeled with 6-carboxyfluorescein (FAM) and 6-carboxytetramethylrhodamine (TAMRA) (5'-FAM-CTT AAA TAY TAT GAT TGG GAY CCC CA-TAMRA-3' (SEQ ID NO:6), and 450 nM of each starter (5'-CAA CCT GCG CTA ACG-3' (SEQ ID NO:4) and 5'-TCC CAY ACA GTT CCA AAT T-3' (SEQ ID NO:5)). The aforementioned specific probe and primers were used to amplify a 151 bp fragment of sequence derived from the FCV genome to measure the number of viral RNA copies in the sample [63]. The reaction was carried out in a thermocycler (CFX96 Touch™ Real-197 Time PCR Detection System, Bio-Rad) under the following conditions: 3 min at 95° C., then 39 cycles of 15 seconds at 95° C. and 30 seconds at 51° C.

Appropriate standards were prepared to evaluate the initial number of viral RNA molecules in the sample. The cDNA-transcribed sequence fragment was amplified using the primers described above. The DNA thus obtained was cloned into the pTZ57R/T plasmid (Thermo Scientific, Poland) using the InsTAclone PCR Cloning Kit (Thermo Scientific, Poland). Transformation of *E. coli* TOP10 strain (Life Technologies, Poland) and propagation of the plasmid vector in a standard manner was performed. The plasmid was then purified using the GeneJET Plasmid Miniprep Kit (Thermo Scientific, Poland) and subjected to linearization by digestion with KpnI restriction enzyme. The concentration of linearized DNA was assessed by spectrophotometric measurement and the number of copies per milliliter was calculated. Eight 10-fold serial dilutions were used as the template for real-time PCR. The ability of polymers to inhibit FCV replication was determined as a decrease in viral RNA copy number as a function of logarithm per milliliter of medium.

b) Plaque Assays

Quantitative analysis of FCV infectious virions was carried out by plaque assays using low melting agarose. 10-fold serial dilutions of collected supernatants were prepared, then applied to the cells and incubated for 1 hour. Then, the medium was removed and 0.6% liquid agarose mixed with the DMEM culture medium was applied to the cells. Plates were incubated at room temperature for about 20 minutes, and then the plates were transferred to the incubator. The time necessary for plaques to form was about 24 hrs. After this time, the cells were fixed for a minimum of 12 h (the time needed to penetrate the agarose) with a solution of 4% formaldehyde, and then stained with a 0.1% solution of crystal violet dissolved in 50% (v/v) methanol:water. Plaques were counted and plotted as the number of PFU (plaque forming unit) per ml.

The conducted research have shown that the polymers tested exhibit antiviral activity and inhibit FCV replication. A positive relationship between antiviral activity and polymer molecular weight has been demonstrated. The results are summarized in FIG. 9.

Example 11

The relationship between the antiviral activity of sodium polystyrene sulfonate (PSSNa) and its concentration in the medium To determine the $IC_{50}$ of sodium salt of polystyrene sulfonate (PSSNa), effect of various concentrations of this polymer on viral infection was tested. This test was carried out analogously to Example 10. The relationship between polymer concentration and its activity against FCV was investigated. Briefly, the number of viral RNA copies per ml was determined by RT-qPCR (FIG. 10 A, FIG. 10 B), while plaque assays allowed to determine the number of infectious virions (FIG. 10 C, FIG. 10 D). The test was carried out using polymers with a molecular weight of 93.5 kDa (FIG. 10 A, FIG. 10 C) and 780 kDa (FIG. 10 B, FIG. 10 D) at various concentrations. The values have been normalized to the viral control.

The calculated $IC_{50}$ values are shown in Table 5 below.

TABELA 5

| $IC_{50}$ values determined for polymers by real-time RT-qPCR and plaque assay | | |
|---|---|---|
| | $IC_{50} \pm SD$ [µg/ml] | |
| Polymer | RT-qPCR | Plaque assay |
| $PSSNa_{93.5}$ | 42.75 ± 2.46 | 49.51 ± 0.14 |
| $PSSNa_{780}$ | 9.72 ± 1.05 | 10.47 ± 1.47 |

The conducted research have shown that the polymers tested have antiviral activity and inhibit the replication of FCV at low, non-toxic concentrations.

Example 12

Determination of the antiviral mechanism of action of PSSNa polymers

To determine the mechanism of action of the PSSNa polymer and identify the stage at which PSSNa inhibits FCV-induced cell infection, the 4 functional tests described below were carried out at a polymer concentration of 200 µg/ml.

Test I (Inactivation Test)

The concentrated virus suspension was incubated with the polymer for 1 hour at 22° C. with shaking, and then the samples were diluted to reduce the polymer concentration below the range of concentrations in which it is active. Virus titers were assessed using a plaque assay.

Test I allows to determine whether inhibition occurs through the interaction between the polymer and the virus, in other words, it allows to determine whether the test compound has a direct effect on the virus.

Test II (Cell Protection Test)

Fully confluent CrFK cells were incubated in the presence or absence of the polymer for 1 hour at 37° C. The plates were then washed twice with 1×PBS to remove unbound polymer particles, after which fresh medium without virus (control sample) or with virus (400 $TCID_{50}$/ml) was added to each well in equal volume and incubated for 1.5 hrs at 37° C. The plates were then washed twice with 1×PBS to remove unbound viral particles. Fresh medium was applied to the cells and they were incubated for 18 hrs at 37° C. Finally, culture supernatant was collected to assess replication efficiency by quantifying infectious viral particle number and viral RNA copy number using plaque assays and RT-qPCR reactions, respectively.

This test determines whether the polymer by e.g. binding to cell surfaces is able to "protect" them from infection by preventing interaction with the entry receptor.

Test III (Adhesion Test)

This test was carried out at 4° C. at which intracellular transport is inhibited. Briefly, completely confluent CrFK cells were cooled at 4° C. for 20 min. Subsequently, fresh medium without virus (control sample) or with virus (400 $TCID_{50}$/ml) with or without polymer was applied to the cells. Plates were incubated for 1 hour at 4° C. Intracellular transport at this temperature was stopped, whereas adsorption of viruses to cell receptors was possible. After incubation, the cells were washed twice with ice-cold 1×PBS to remove unbound viral particles and unbound polymer, fresh medium was added and the cells were incubated for 18 hrs at 37° C. After 18 h the supernatant was collected and the number of viral particles was quantified using RT-qPCR and plaque assays.

This test allows to determine whether inhibition occurs through the competition of the polymer with the virus for the adhesive agent and/or whether the polymer, interacting with the adhesive agent, prevents its interaction with the virus.

Test IV (Late Stages: Replication, Assembly and Release)

In this test, infection was first carried out by incubating the cells with the virus, and only after infection was the polymer applied. Fresh medium containing a non-infectious sample or a virus sample (400 $TCID_{50}$/ml) was applied to confluent CrFK cells, then the plates were incubated for 1.5 h at 37° C. After incubation, the wells were washed twice with PBS to remove unbound viral particles, then fresh medium containing the selected polymer concentration was added to each well. Plates were incubated for 18 hrs at 37° C. After 18 h supernatants were collected, then separately PBS was added to the wells and cells were subjected to two freeze-thaw cycles to obtain cell lysates, then virus replication was assessed quantified using plaque assays and RT-qPCR.

This test allows to determine whether the inhibition of the spread of the virus occurs at late stages of infection, e.g. replication, assembly or release.

After performing each of the functional tests, the cells were incubated for 18 hrs at 37° C. After this time, the supernatant (and cell lysate in the case of test IV) was collected and plaque and RT-qPCR tests were performed in real time to identify the stage at which infection is inhibited. The exception was test I, for which, for technical reasons, only plaque tests could be performed.

In the tests described above, the number of viral RNA copies in 1 ml of medium was determined by real-time RT-qPCR (FIG. 11A), whereas plaque assays allowed to determine the number of infectious virions in the sample (FIG. 11B). The tests were carried out using different concentrations of polymers with a molecular weight of 93.5 kDa (FIG. 11 C) and 780 kDa (FIG. 11 D).

As a result of the research, it was found that PSSNa polymers exhibit antiviral activity at late stages of infection (IV test), probably at the stage of viral replication. The antiviral efficacy of polymers with a molecular weight of 93.5 kDa and 780 kDa in the late stages of infection was similar, whereas the polymer with a higher molecular weight in the general test (FIG. 11) is more effective, indicating a possible additional mechanism of its action. This observation is consistent with the results for test III, which indicate that a higher molecular weight polymer inhibits viral infection also in the early stages of infection, at the stage of virus adhesion to the cell surface, while the lower molecular weight polymer did not have the ability to inhibit the virus at this stage (FIG. 11 C, FIG. 11 D).

Example 13

Visualization of inhibition of early stages cell infection by FCV by PSSNa polymer with molecular mass of 93.5 kDa and 780 kDa by confocal microscopy To make preparations for imaging using a confocal microscope, CrFK cells were plated on microscope slides 24 hrs before experiment. The cells were then cooled and incubated for one hour at 4° C. in the presence of virus or virus and polymer, in a standard manner. After a given incubation time, the unbound viral particles were washed away, the preparations fixed and stained in a standard manner. For immunofluorescence staining, primary antibodies directed against the FCV capsid protein (catalog number: sc-80785, Santa Cruz CA, USA) were used, followed by secondary antibodies conjugated with Alexa Fluor 488 (Invitrogen, Poland) to visualize virions, Alexa-conjugated phalloidin Fluor 647 (Invitrogen, Poland) for staining F-actin and DAPI (Sigma-Aldrich, Poland) for staining nuclear DNA. Maximum projections were presented.

FIG. 12 shows a visualization of the inhibition of FCV-induced CrFK cell infection by PSSNa polymers. The signal for each color (blue, red and green channels) and the combination of signals from all three dyes (combined channels) are presented separately. Cell nuclei (nuclear DNA) are shown in blue, F-actin is shown in red, and FCV virions are shown in green. The figure shows visualizations of uninfected control cells, viral control, 1000 μg/ml PSSNa93.5 treated cells and 1000 μg/ml PSSNa780 treated cells. The scale bar corresponds to 10 μm.

Microscopic visualizations show a significant decrease in the number of FCV virions present in CrFK cells in the presence of the PSSNa polymer with a high molecular weight of 780 kDa, while the decrease in the number of FCV virions after using a polymer with a molecular weight of 93.5 kDa is not noticeable. The study confirms the effectiveness of the sulfonated polystyrene derivative, in particular the high molecular weight, in inhibiting FCV-induced infection also in the early stages of infection.

Example 14

Quantitative analysis of inhibition of early stages of cell infection after incubation with or without PSSNa polymer with a molecular weight of 93.5 kDa and 780 kDa Representative microscopic images in Example 13 were quantified in ImageJ Fiji and the number of FCV F9 virions per cell counted—both internalized and cell surface adhering particles. It was shown that after the cell protection test (test II) the number of FCV F9 virions did not decrease in the presence of polymer, which is consistent with previously obtained results. It was also confirmed that after performing the adhesion test (test III) a statistically significant decrease in the number of viruses per cell was noticeable compared to the viral control, but only in the case of a polymer with a higher molecular weight. The results for each of the systems are presented as mean counts of 10 CrFK cells. Quantitative analysis of microscopic images showed that a polymer with a molecular weight of 780 kDa also inhibited infection at early stages of infection. For a polymer with a molecular weight of 93.5 kDa, there was no statistically significant difference between the control cells and those incubated with the inhibitor. The obtained percentage analysis of virus counts per cell is consistent with microscopic observations.

Example 15

The effect of sodium polystyrene sulfonate (PSSNa) on infectivity of FCV clinical strains Veterinary strains were obtained thanks to the kindness of veterinarians at the 'Ambuvet' veterinary clinic and at the Homeless Animal Shelter in Krakow, who took swabs from cats showing symptoms of upper respiratory tract infection. Swabs were taken from the throat and nasal cavity using special swab sticks for transporting viral clinical samples. To eliminate possible bacterial and fungal infection, the samples were filtered using sterile, disposable filters with a pore diameter of 0.2 which should not be a barrier for caliciviruses with a diameter of about 35 nm. The filtered transport medium was transferred to a 12-well plate with confluent CrFK cells. Plates were incubated up to 96 hours, monitoring the wells twice a day. If the cytopathic effect (CPE) was visible, the supernatant was taken for plaque assays (procedure described in Example 10b). After 24 hours, single, well-visible plaques were selected and agar pierced at this site with a sterile pipette tip. The tip was then transferred and the medium was touched with it on a new 12-well plate containing fully confluent CrFK cells. If a cytopathic effect occurred, the supernatant was transferred and aliquoted to new freezing tubes and stored at −80° C. The species affiliation of each strain was confirmed by sequence fragment sequencing for the main VP1 capsid protein. The origin of six veterinary strains (FCV K1, K2, K3, K5, K8 and K10) are characterized in Table 6.

TABLE 6

Origin of the FCV clinical strains.

| Strain | Collection date | Cat's gender | Cat's age | Place of swab collection | Disease symptoms | The origin of the swab |
| --- | --- | --- | --- | --- | --- | --- |
| FCV K1 | Sep. 27, 2018 | ♂ | 3 months | Throat | Upper respiratory tract infection, sneezing | Ambuvet veterinary clinic |
| FCV K2 | Aug. 10, 2018 | ♀ | 6 months | Throat | Upper respiratory tract infection, purulent discharge | Ambuvet veterinary clinic |

TABLE 6-continued

Origin of the FCV clinical strains.

| Strain | Collection date | Cat's gender | Cat's age | Place of swab collection | Disease symptoms | The origin of the swab |
|---|---|---|---|---|---|---|
| FCV K3 | Aug. 11, 2018 | ♂ | 3 years | Throat | Recurrent upper respiratory tract infection from the eyes | Ambuvet veterinary clinic |
| FCV K5 | Nov. 25, 2018 | ♀ | 6 months | Throat | Upper respiratory tract infection, purulent discharge from the eyes | Shelter for homeless animals in Krakow |
| FCV K8 | Nov. 25, 2018 | ♂ | 9 months | Nasal cavity | Upper respiratory tract infection, purulent discharge from the nose | Shelter for homeless animals in Krakow |
| FCV K10 | Nov. 25, 2018 | ♀ | 3 months | Throat | Upper respiratory tract infection | Shelter for homeless animals in Krakow |

In order to determine the antiviral activity of sodium polystyrene sulfonate (PSSNa) against isolated FCV clinical strains, the effect of different concentrations of this polymer with two selected molecular weights (93.5 kDa and 780 kDa) on viral infection was tested. The viral replication assay was carried out analogously to Example 9. Briefly, viral RNA copies per ml were determined by reverse transcription and quantitative real-time PCR, while plaque assays allowed to determine the number of infectious virions (FIG. 14). The values were normalized to the viral control, i.e. infected cells not incubated with the polymer.

The conducted research confirmed that the polymers tested have antiviral activity against all isolated FCV clinical strains at low, non-toxic concentrations. The replication of each of the clinical strains was reduced by at least 20 times (FCV K1 strain), while in the case of two strains (FCV K5 and K10) the infection was completely inhibited. A positive relationship between antiviral activity and molecular weight was demonstrated, identically to that of the FCV F9 laboratory strain, for which the results are shown in Example 10.

Example 16

Interaction test: analysis of FCV virus binding ability to surfaces coated with PSSNa polymer, analysis of direct virus-polymer interaction.

The interaction test allows to determine if there is a direct interaction between the inhibitor and the virus. Sterile cover slips were placed inside a 12-well plate. To compensate for the negative charge of coverslips, they were incubated with 3% FBS or bovine collagen (Purecol) in PBS for 2 hrs at 37° C., slides incubated in PBS were the control. The slides were then washed twice with PBS and a PBS solution or polymer at a concentration of 20 µg/ml was added in an amount of 1 ml per well. Samples were incubated for 2 hrs at 37° C. This step is to cover the slides with a negatively charged polymer. Then, the unbound polymer particles were washed away with PBS solution. The next step was incubation of slides with a viral suspension of $TCID_{50}$ equal to 13,000,000/ml or control for 2 hrs at 37° C. It was assumed that if there is a direct interaction between the polymer and the virus, the virions will bind to the surface covered with the polymer. Unbound particles were washed away with PBS solution and the material was prepared for confocal microscopy imaging. Immunofluorescent staining was performed, preparations were visualized, and then the number of viral particles per confocal plane was counted in ImageJ Fiji.

For slides coated with PSSNa 780 kDa, the number of virions was much higher than for slides not coated with polymer or coated with PSSNa 93.5 kDa. It is worth noting that for slides coated with FBS and coated with PSSNa93.5, a statistically significant increase in the number of virions per confocal plane was also shown, however, it was much smaller than in the case of PSSNa780. The above results indicate that PSSNa 780 kDa interacts directly with the viral particle, but the influence of this interaction on FCV infectivity is unknown.

Example 17

Determination of the in vitro antiviral activity of the PEG-PSSNa hydrogel

The aim of the study was to determine the formulation in which PSSNa can be applied to the animal's skin, and then to determine the effect of the formulation on the infection process and transdermal toxicity of the formulation.

The first stage determined the highest non-toxic concentration of polyethylene glycol with a molecular weight of 400 Da (PEG, Sigma-Aldrich, Poland, Mw=400) (PEG400)), which can be used for in vitro experiments using the CrFK cell line. For this purpose, 8 solutions of PEG polymer with concentrations: 100, 50, 40, 30, 25, 20, 15 and 10 mg/ml were prepared. Cells were incubated with the polymer at a specific concentration for 48 hrs, followed by an XTT assay analogous to previous examples. Concentrations above 30 mg/ml have been shown to be toxic to CrFK cells and cannot be used in further experiments. Therefore, in further studies it was decided to use the highest, non-toxic PEG400 concentration of 30 mg/ml. Cytotoxicity results normalized to control (polymer-untreated cells) are shown in FIG. 16 A.

To prepare the PSSNa-PEG hydrogel, the 1000 kDa PSSNa (PSSNa1000 kDa) was dissolved in water and then added dropwise to the PEG400 solution diluted in DMEM culture medium. The final concentration of PSSNa1000 kDa in the solution was 200 m/ml, while the concentration of PEG400 was 30 mg/ml.

In order to verify that the hydrogel alone does not affect the antiviral activity of the active substance PSSNa, a viral replication test was performed. Briefly, CrFK cells were infected in the presence of a hydrogel before, during and after infection. The experiments were carried out analogously as described in the previous examples. Cells were incubated for 18 hrs (FCV infection) or 48 hrs (FHV-1 infection). After this time, the supernatant was collected, followed by real-time PCR and virus titers were checked by plaque assays. The results obtained are shown in FIG. 16 for the FHV-1 virus (B, C) and for the FCV virus (D, E).

It has been demonstrated that the composition of the hydrogel is not toxic and does not affect the antiviral activity of the sodium polystyrene sulfonate Example 18

Determination of the dermal toxicity of sodium polystyrene sulfonate in a mouse model The aim of the experiment was to determine the maximum non-toxic dermal dose of sodium polystyrene sulfonate in a mouse model. The test material was 6-week-old female mice of the BALB/c strain obtained from the Experimental Medicine Center of the Medical University of Bialystok. The consent for the experiment No. 281/2018 was obtained from the 2nd Local Ethical Commission for Animal Experiments in Krakow at the Institute of Pharmacology of the Polish Academy of Sciences. The animals were quarantined for 5 days. After the quarantine, a general medical and veterinary examination was performed.

During quarantine and experiment, the animals stayed in rooms with controlled parameters: temperature 22° C.±2° C., humidity 55%±5% and lighting: artificial, photoperiod: 12 hours of light/12 hours of darkness. Maintenance feed from Altromin was used. Only healthy individuals selected at random were qualified for the experiment. The animals were divided into groups, in each experiment the group contained 5 individuals: control group—saline, experimental group—PSSNa 50 mg/ml, experimental group—PSSNa 75 mg/ml, experimental group—PSSNa 100 mg/ml.

The test material was applied directly to the shaved dorsal skin in a volume of 100 µl/mouse, once a day for 7 days. Detailed clinical observations were made daily from the day of administration of the compound. Measurement of animal body weight was carried out before administration of the test material and daily during the observation. At the end of the experiment, the animals were subjected to euthanasia. Necropsies were carried out and blood was collected for biochemical analysis.

The PSSNa-PEG hydrogel was prepared by mixing PEG with a molecular weight of 400 Da with water (in a 9:1 ratio, volume/volume). PSSNa was dissolved in water and then added dropwise to the PEG solution. Dermal toxicity analysis was performed using a hydrogel with a PSSNa concentration of 50, 75 and 100 mg/ml. After 5 days of quarantine, the mice were shaved on the lateral side of the back, and then 100 µl hydrogel or saline was applied to the shaved skin. The experiment lasted 7 days, the hydrogel was applied daily. Mice were weighed and monitored every day (daily weight measurements are shown in Tables 7a-b). After 7 days, the remaining mice were euthanized by cervical dislocation. The skin at the hydrogel injection site was closely monitored for redness, ulceration or other skin lesions each day according to the following health scale:

0—good health, no obvious symptoms
1—apathy, fur raised
2—hunched silhouette, slight weight loss
3—anorexia, increased breathing effort and further weight loss
4—agony
5—death Health results are shown in Tables 8a-b.

After animal euthanasia, blood, liver, kidney and spleen were collected for further analysis. Biochemical analysis included GLU (mg/dl), BUN (mg/dl), ALP (IU/L), TP (g/dl), GPT (IU/L) and CRE (mg/dl). The results of biochemical analyzes are presented in Tables 9a-b.

In animal studies, polystyrene sulfonate after administration directly to the skin at a 50, 75 and 100 mg/ml did not cause clinical symptoms. Clinical symptoms were not observed during biochemical tests and weight measurement in animals. After necropsies, no macroscopic changes in organs were found.

Sodium polystyrene sulfonate administered for 7 days on the skin in the form of a hydrogel with PEG polymer at a dose of 50, 75 and 100 mg/ml is not toxic to animals and can be used in the future for testing antiviral activity in animals.

TABLE 7a

Measurement of mouse body weight during the experiment (December 2018)

| Day | 0 | 1 | 2 | 3 | 4 | 5 | 6 |
|---|---|---|---|---|---|---|---|
| Control group (saline) | | | | | | | |
| 909 | 21.2 | 21.5 | 21.0 | 21.4 | 22.0 | 22.1 | 21.8 |
| 450 | 20.4 | 20.3 | 19.7 | 20.5 | 21.0 | 20.7 | 21.0 |
| 449 | 20.5 | 20.5 | 21.0 | 21.5 | 20.9 | 21.0 | 21.2 |
| 448 | 20.1 | 19.5 | 20.0 | 19.7 | 20.0 | 19.8 | 19.7 |
| 447 | 20.4 | 20.5 | 20.5 | 19.5 | 19.0 | 19.4 | 19.2 |
| PSSNa group (50 mg/ml) | | | | | | | |
| 436 | 19.7 | 20.1 | 20.2 | 19.6 | 19.6 | 19.7 | 19.0 |
| 437 | 21.0 | 21.6 | 22.2 | 21.9 | 21.9 | 22.0 | 22.3 |
| 438 | 23.1 | 23.0 | 23.5 | 23.0 | 22.7 | 22.5 | 22.7 |
| 439 | 20.9 | 21.3 | 21.0 | 21.3 | 20.9 | 21.0 | 21.1 |
| 440 | 21.9 | 21.3 | 21.1 | 21.4 | 21.8 | 21.6 | 21.3 |
| PSSNa group (75 mg//ml) | | | | | | | |
| 441 | 22.6 | 22.3 | 22.0 | 22.5 | 22.6 | 22.5 | 22.3 |
| 442 | 21.5 | 21.0 | 21.8 | 20.6 | 20.7 | 20.6 | 20.7 |
| 443 | 20.4 | 20.7 | 20.6 | 20.6 | 20.7 | 20.2 | 20.6 |
| 444 | 22.8 | 22.5 | 22.5 | 23.0 | 23.1 | 22.9 | 22.8 |
| 445 | 22.1 | 22.5 | 22.4 | 22.1 | 22.3 | 22.0 | 21.8 |
| PSSNa group (100 mg/ml) | | | | | | | |
| 446 | 25.2 | 25.5 | 25.4 | 25.0 | 25.1 | 25.4 | 24.8 |
| 401 | 21.6 | 22.1 | 22.0 | 22.1 | 22.2 | 22.1 | 21.6 |
| 402 | 22.2 | 22.2 | 22.9 | 22.7 | 23.0 | 22.9 | 22.6 |
| 403 | 22.1 | 21.7 | 21.9 | 21.7 | 21.9 | 21.8 | 22.0 |
| 404 | 22.3 | 21.8 | 21.8 | 21.6 | 21.9 | 22.0 | 21.6 |

TABLE 7b

Measurement of mouse body weight during the experiment (January 2019)

| Day | 0 | 1 | 2 | 3 | 4 | 5 | 6 |
|---|---|---|---|---|---|---|---|
| Control group (saline) | | | | | | | |
| 561 | 19.8 | 19.9 | 20.0 | 20.2 | 20.1 | 20.4 | 20.5 |
| 562 | 18.2 | 18.2 | 18.0 | 18.1 | 18.1 | 18.0 | 18.3 |
| 563 | 19.0 | 19.0 | 18.9 | 19.2 | 19.0 | 19.1 | 19.1 |
| 564 | 19.5 | 19.9 | 19.4 | 19.5 | 19.4 | 19.6 | 19.5 |
| 565 | 17.8 | 18.2 | 18.1 | 18.3 | 18.3 | 18.4 | 18.5 |

TABLE 7b-continued

Measurement of mouse body weight during the experiment (January 2019)

| Day | 0 | 1 | 2 | 3 | 4 | 5 | 6 |
|---|---|---|---|---|---|---|---|
| PSSNa group (50 mg/ml) | | | | | | | |
| 566 | 19.2 | 19.4 | 19.7 | 19.9 | 19.9 | 20.0 | 20.1 |
| 567 | 18.3 | 18.3 | 18.4 | 18.3 | 18.4 | 18.6 | 18.7 |
| 568 | 19.7 | 19.8 | 20.0 | 20.0 | 20.2 | 20.3 | 20.3 |
| 569 | 18.9 | 19.1 | 19.7 | 19.8 | 19.9 | 20.0 | 20.1 |
| 570 | 19.9 | 20.3 | 20.6 | 20.8 | 21.1 | 21.2 | 21.3 |
| PSSNa group (75 mg/ml) | | | | | | | |
| 660 | 18.4 | 18.6 | 19.2 | 19.4 | 19.4 | 19.6 | 19.5 |
| 661 | 19.2 | 19.7 | 19.9 | 20.1 | 19.8 | 19.9 | 20.1 |
| 662 | 19.3 | 19.7 | 20.1 | 20.1 | 20.4 | 20.3 | 20.3 |
| 663 | 18.8 | 19.0 | 19.3 | 19.6 | 19.8 | 19.8 | 19.9 |
| 664 | 18.5 | 18.9 | 19.1 | 19.3 | 19.4 | 19.5 | 19.6 |
| PSSNa group (100 mg/ml) | | | | | | | |
| 655 | 19.7 | 19.6 | 19.9 | 19.8 | 19.9 | 19.9 | 20.0 |
| 656 | 18.0 | 18.2 | 18.5 | 18.6 | 18.8 | 18.8 | 18.9 |
| 657 | 17.3 | 17.4 | 17.9 | 18.1 | 18.3 | 18.5 | 18.4 |
| 568 | 18.8 | 19.0 | 19.4 | 19.6 | 19.6 | 19.7 | 19.8 |
| 659 | 17.0 | 17.5 | 17.9 | 17.9 | 18.1 | 18.2 | 18.4 |

TABLE 8a

Clinical observations during the experiment (December 2018)

| Day | 0 | 1 | 2 | 3 | 4 | 5 | 6 |
|---|---|---|---|---|---|---|---|
| Control group (saline) | | | | | | | |
| 909 | 0 | 0 | 0 | 0 | 0 | 0 | 0 |
| 450 | 0 | 0 | 0 | 0 | 0 | 0 | 0 |
| 449 | 0 | 0 | 0 | 0 | 0 | 0 | 0 |
| 448 | 0 | 0 | 0 | 0 | 0 | 0 | 0 |
| 447 | 0 | 0 | 0 | 0 | 0 | 0 | 0 |
| PSSNa group (50 mg/ml) | | | | | | | |
| 436 | 0 | 0 | 0 | 0 | 0 | 0 | 0 |
| 437 | 0 | 0 | 0 | 0 | 0 | 0 | 0 |
| 438 | 0 | 0 | 0 | 0 | 0 | 0 | 0 |
| 439 | 0 | 0 | 0 | 0 | 0 | 0 | 0 |
| 440 | 0 | 0 | 0 | 0 | 0 | 0 | 0 |
| PSSNa group (75 mg//ml) | | | | | | | |
| 441 | 0 | 0 | 0 | 0 | 0 | 0 | 0 |
| 442 | 0 | 0 | 0 | 0 | 0 | 0 | 0 |
| 443 | 0 | 0 | 0 | 0 | 0 | 0 | 0 |
| 444 | 0 | 0 | 0 | 0 | 0 | 0 | 0 |
| 445 | 0 | 0 | 0 | 0 | 0 | 0 | 0 |
| PSSNa group (100 mg/ml) | | | | | | | |
| 446 | 0 | 0 | 0 | 0 | 0 | 0 | 0 |
| 401 | 0 | 0 | 0 | 0 | 0 | 0 | 0 |
| 402 | 0 | 0 | 0 | 0 | 0 | 0 | 0 |
| 403 | 0 | 0 | 0 | 0 | 0 | 0 | 0 |
| 404 | 0 | 0 | 0 | 0 | 0 | 0 | 0 |

TABLE 8b

Clinical observations during the experiment (January 2019)

| Day | 0 | 1 | 2 | 3 | 4 | 5 | 6 |
|---|---|---|---|---|---|---|---|
| Control group (saline) | | | | | | | |
| 561 | 0 | 0 | 0 | 0 | 0 | 0 | 0 |
| 562 | 0 | 0 | 0 | 0 | 0 | 0 | 0 |
| 563 | 0 | 0 | 0 | 0 | 0 | 0 | 0 |
| 564 | 0 | 0 | 0 | 0 | 0 | 0 | 0 |
| 565 | 0 | 0 | 0 | 0 | 0 | 0 | 0 |
| PSSNa group (50 mg/ml) | | | | | | | |
| 566 | 0 | 0 | 0 | 0 | 0 | 0 | 0 |
| 567 | 0 | 0 | 0 | 0 | 0 | 0 | 0 |
| 568 | 0 | 0 | 0 | 0 | 0 | 0 | 0 |
| 569 | 0 | 0 | 0 | 0 | 0 | 0 | 0 |
| 570 | 0 | 0 | 0 | 0 | 0 | 0 | 0 |
| PSSNa group (75 mg//ml) | | | | | | | |
| 660 | 0 | 0 | 0 | 0 | 0 | 0 | 0 |
| 661 | 0 | 0 | 0 | 0 | 0 | 0 | 0 |
| 662 | 0 | 0 | 0 | 0 | 0 | 0 | 0 |
| 663 | 0 | 0 | 0 | 0 | 0 | 0 | 0 |
| 664 | 0 | 0 | 0 | 0 | 0 | 0 | 0 |
| PSSNa group (100 mg/ml) | | | | | | | |
| 655 | 0 | 0 | 0 | 0 | 0 | 0 | 0 |
| 656 | 0 | 0 | 0 | 0 | 0 | 0 | 0 |
| 657 | 0 | 0 | 0 | 0 | 0 | 0 | 0 |
| 568 | 0 | 0 | 0 | 0 | 0 | 0 | 0 |
| 659 | 0 | 0 | 0 | 0 | 0 | 0 | 0 |

TABLE 9a

Biochemical analysis results after animal euthanasia (December 2018)

| Measured parameter | BUN [mg/dl] | Glu [mg/dl] | ALP (IU/L) | T-Pro [g/dl] | GPT [IU/L] | Cre [mg/dl] |
|---|---|---|---|---|---|---|
| Control group (saline) | | | | | | |
| 909 | 23 | 140 | 48 | 4.2 | 2 | 1.0 |
| 450 | 19 | 149 | 77 | 4.6 | 16 | 0.9 |
| 449 | 21 | 137 | 56 | 4.5 | 10 | 0.8 |
| 448 | 22 | 140 | 50 | 4.8 | 6 | 0.9 |
| 447 | 26 | 140 | 80 | 4.6 | 1 | 1.0 |
| PSSNa group (50 mg/ml) | | | | | | |
| 436 | 22 | 129 | 95 | 4.4 | 9 | 0.7 |
| 437 | 20 | 133 | 84 | 4.8 | 10 | 0.8 |
| 438 | 26 | 128 | 67 | 4.2 | 6 | 0.7 |
| 439 | 19 | 130 | 60 | 4.5 | 10 | 1.0 |
| 440 | 20 | 128 | 48 | 4.2 | 9 | 1.0 |
| PSSNa group (75 mg/ml) | | | | | | |
| 441 | 26 | 131 | 89 | 4.7 | 4 | 0.9 |
| 442 | 20 | 143 | 86 | 4.2 | 7 | 0.7 |
| 443 | 17 | 138 | 68 | 4.3 | 10 | 0.8 |
| 444 | 23 | 150 | 62 | 4.8 | 3 | 0.9 |
| 445 | 23 | 139 | 75 | 4.2 | 2 | 0.9 |
| PSSNa group (100 mg/ml) | | | | | | |
| 446 | 15 | 139 | 73 | 4.3 | 7 | 0.9 |
| 401 | 20 | 123 | 62 | 4.4 | 10 | 0.8 |
| 402 | 17 | 134 | 80 | 4.8 | 9 | 0.9 |
| 403 | 25 | 129 | 93 | 4.2 | 3 | 0.9 |
| 404 | 26 | 137 | 88 | 4.6 | 6 | 0.8 |

TABLE 9b

Biochemical analysis results after animal euthanasia (January 2019)

| Measured parameter | BUN [mg/dl] | Glu [mg/dl] | ALP (IU/L) | T-Pro [g/dl] | GPT [IU/L] | Cre [mg/dl] |
|---|---|---|---|---|---|---|
| Control group (saline) | | | | | | |
| 561 | 28 | 128 | 85 | 4.6 | 5 | 1.1 |
| 562 | — | 126 | 77 | 4.1 | 18 | 0.8 |
| 563 | 17 | 124 | 46 | 4.3 | 4 | 0.8 |
| 564 | 26 | 140 | 47 | 4.5 | 4 | 0.8 |
| 565 | 25 | 183 | 44 | 4.6 | 1 | 1.0 |
| PSSNa group (50 mg/ml) | | | | | | |
| 566 | 19 | 120 | 109 | 4.2 | 7 | 0.8 |
| 567 | 15 | 126 | 44 | 4.1 | 6 | 0.9 |
| 568 | 24 | 140 | 77 | 4.6 | 3 | 0.9 |
| 569 | 28 | 129 | 64 | 4.9 | 12 | 1.0 |
| 570 | 28 | 131 | 50 | 4.9 | 6 | 1.0 |
| PSSNa group (75 mg/ml) | | | | | | |
| 660 | 27 | 128 | 80 | 4.8 | 6 | 1.0 |
| 661 | 26 | 122 | 72 | 4.2 | 9 | 0.8 |
| 662 | 20 | 138 | 56 | 4.6 | 10 | 0.9 |
| 663 | 28 | 126 | 64 | 4.7 | 5 | 0.9 |
| 664 | 23 | 124 | 48 | 4.5 | 8 | 0.8 |
| PSSNa group (100 mg/ml) | | | | | | |
| 655 | 19 | 150 | 56 | 4.4 | 8 | 1.0 |
| 656 | 24 | 130 | 76 | 4.8 | 11 | 1.0 |
| 657 | 17 | 138 | 82 | 4.1 | 4 | 0.8 |
| 658 | 22 | 122 | 54 | 4.3 | 2 | 0.8 |
| 659 | 27 | 128 | 62 | 4.6 | 9 | 0.9 |

LITERATURE

1. Helps, C. R. et al., Factors associated with upper respiratory tract disease caused by feline herpesvirus, feline calicivirus, Chlamydophila felis and Bordetella bronchiseptica in cats: experience from 218 European catteries. Vet Rec, 2005. 156(21): pp. 669-73.
2. Binns, S. H. et al., A study of feline upper respiratory tract disease with reference to prevalence and risk factors for infection with feline calicivirus and feline herpesvirus. J Feline Med Surg, 2000. 2(3): pp. 123-33.
3. Bannasch, M. J. and J. E. Foley, Epidemiologic evaluation of multiple respiratory pathogens in cats in animal shelters. J Feline Med Surg, 2005. 7(2): pp. 109-19.
4. Fernandez, M. et al., Prevalence of feline herpesvirus-1, feline calicivirus, Chlamydophila felis and Mycoplasma felis DNA and associated risk factors in cats in Spain with upper respiratory tract disease, conjunctivitis and/or gingivostomatitis. J Feline Med Surg, 2017. 19(4): pp. 461-469.
5. Cohn, L. A., Feline respiratory disease complex. Vet Clin North Am Small Anim Pract, 2011. 41(6): pp. 1273-89.
6. Fields B N, K. D., Howley P M, Fields virology. 6th ed., ed. W. K. Health/Lippincott and W. Wilkins. 2013.
7. Xu, F. et al., Seroprevalence and coinfection with herpes simplex virus type 1 and type 2 in the United States, 1988-1994. J Infect Dis, 2002. 185(8): pp. 1019-24.
8. Gaskell, R. M. and R. C. Povey, Experimental induction of feline viral rhinotracheitis virus re-excretion in FVR-recovered cats. Vet Rec, 1977. 100(7): pp. 128-33.
9. Maggs, D. J. et al., Evaluation of serologic and viral detection methods for diagnosing feline herpesvirus-1 infection in cats with acute respiratory tract or chronic ocular disease. J Am Vet Med Assoc, 1999. 214(4): pp. 502-7.
10. Gould, D., Feline herpesvirus-1: ocular manifestations, diagnosis and treatment options. J Feline Med Surg, 2011. 13(5): pp. 333-46.
11. Hartley, C., Aetiology of corneal ulcers assume FHV-1 unless proven otherwise. J Feline Med Surg, 2010. 12(1): pp. 24-35.
12. Bistner, S. I. et al., Ocular manifestations of feline herpesvirus infection. J Am Vet Med Assoc, 1971. 159(10): pp. 1223-37.
13. Stiles, J., Feline herpesvirus. Clin Tech Small Anim Pract, 2003. 18(3): pp. 178-85.
14. Gaskell, R. M. and R. C. Povey, Re-excretion of feline viral rhinotracheitis virus following corticosteroid treatment. Vet Rec, 1973. 93(7): pp. 204-5.
15. Nasisse, M. P. et al., Isolation of feline herpesvirus 1 from the trigeminal ganglia of acutely and chronically infected cats. J Vet Intern Med, 1992. 6(2): pp. 102-3.
16. Miller, W. H. and R. L. Miller, Phosphorylation of acyclovir diphosphate by cellular enzymes. Biochem Pharmacol, 1982. 31(23): pp. 3879-84.
17. Miller, W. H. and R. L. Miller, Phosphorylation of acyclovir (acycloguanosine) monophosphate by GMP kinase. J Biol Chem, 1980. 255(15): pp. 7204-7.
18. Elion, G. B., The biochemipy and mechanism of action of acyclovir. J Antimicrob Chemother, 1983. 12 Suppl B: pp. 9-17.
19. Maggs, D. J., Update on pathogenesis, diagnosis, and treatment of feline herpesvirus type 1. Clin Tech Small Anim Pract, 2005. 20(2): pp. 94-101.
20. Maggs, D. J. and H. E. Clarke, In vitro efficacy of ganciclovir, cidofovir, penciclovir, foscarnet, idoxuridine, and acyclovir against feline herpesvirus type-1. Am J Vet Res, 2004. 65(4): pp. 399-403.
21. Nasisse, M. P. et al., In vitro susceptibility of feline herpesvirus-1 to vidarabine, idoxuridine, trifluridine, acyclovir, or bromovinyldeoxyuridine. Am J Vet Res, 1989. 50(1): pp. 158-60.
22. Collins, P., The spectrum of antiviral activities of acyclovir in vitro and in vivo. J Antimicrob Chemother, 1983. 12 Suppl B: pp. 19-27.
23. Soul-Lawton, J. et al., Absolute bioavailability and metabolic disposition of valaciclovir, the L-valyl ester of acyclovir, following oral administration to humans. Antimicrob Agents Chemother, 1995. 39(12): pp. 2759-64.
24. Nasisse, M. P. et al., Effects of valacyclovir in cats infected with feline herpesvirus 1. Am J Vet Res, 1997. 58(10): pp. 1141-4.
25. Hussein, I. T., R. V. Menashy, and H. J. Field, Penciclovir is a potent inhibitor of feline herpesvirus-1 with susceptibility determined at the level of virus-encoded thymidine kinase. Antiviral Res, 2008. 78(3): pp. 268-74.
26. Groth, A. D. et al., In vitro cytotoxicity and antiviral efficacy against feline herpesvirus type 1 of famciclovir and its metabolites. Vet Ophthalmol, 2014. 17(4): pp. 268-74.
27. Thomasy, S. M. et al., Evaluation of orally administered famciclovir in cats experimentally infected with feline herpesvirus type-1. Am J Vet Res, 2011. 72(1): pp. 85-95.
28. Malik, R. et al., Treatment of feline herpesvirus-1 associated disease in cats with famciclovir and related drugs. J Feline Med Surg, 2009. 11(1): pp. 40-8.

29. Filer, C. W. et al., Metabolic and pharmacokinetic studies following oral administration of 14C-famciclovir to healthy subjects. Xenobiotica, 1994. 24(4): pp. 357-68.
30. Pue, M. A. et al., Linear pharmacokinetics of penciclovir following administration of single oral doses of famciclovir 125, 250, 500 and 750 mg to healthy volunteers. J Antimicrob Chemother, 1994. 33(1): pp. 119-27.
31. Hussein, I. T. et al., Substrate specificity and molecular modelling of the feline herpesvirus-1 thymidine kinase. Arch Virol, 2008. 153(3): pp. 495-505.
32. Dalvie, D. et al., Interspecies variation in the metabolism of zoniporide by aldehyde oxidase. Xenobiotica, 2013. 43(5): pp. 399-408.
33. Anderson, R. A. et al., Evaluation of poly(styrene-4-sulfonate) as a preventive agent for conception and sexually transmitted diseases. J Androl, 2000. 21(6): pp. 862-75.
34. Christensen, N. D. et al., Papillomavirus microbicidal activities of high-molecular-weight cellulose sulfate, dextran sulfate, and polystyrene sulfonate. Antimicrob Agents Chemother, 2001. 45(12): pp. 3427-32.
35. Herold, B. C. et al., Poly(sodium 4-styrene sulfonate): an effective candidate topical antimicrobial for the prevention of sexually transmitted diseases.
J Infect Dis, 2000. 181(2): pp. 770-3.
36. Simoes, J. A. et al., Two novel vaginal microbicides (polystyrene sulfonate and cellulose sulfate) inhibit *Gardnerella vaginalis* and anaerobes commonly associated with bacterial vaginosis. Antimicrob Agents Chemother, 2002. 46(8): pp. 2692-5.
37. Zaneveld, L. J. et al., Efficacy and safety of a new vaginal contraceptive antimicrobial formulation containing high molecular weight poly(sodium 4-styrenesulfonate). Biol Reprod, 2002. 66(4): pp. 886-94.
38. Ito, M. et al., In vitro activity of mannan sulfate, a novel sulfated polysaccharide, against human immunodeficiency virus type 1 and other enveloped viruses. Eur J Clin Microbiol Infect Dis, 1989. 8(2): pp. 171-3.
39. Baba, M. et al., Sulfated polysaccharides are potent and selective inhibitors of various enveloped viruses, including herpes simplex virus, cytomegalovirus, vesicular stomatitis virus, and human immunodeficiency virus. Antimicrob Agents Chemother, 1988. 32(11): pp. 1742-5.
40. Mohan, P. et al., Sulfonic acid polymers as a new class of human immunodeficiency virus inhibitors. Antiviral Res, 1992. 18(2): pp. 139-50.
41. Zacharopoulos, V. R. and D. M. Phillips, Vaginal formulations of carrageenan protect mice from herpes simplex virus infection. Clin Diagn Lab Immunol, 1997. 4(4): pp. 465-8.
42. Stiles, J. et al., Effects of lambda-carrageenan on in vitro replication of feline herpesvirus and on experimentally induced herpetic conjunctivitis in cats. Invest Ophthalmol Vis Sci, 2008. 49(4): pp. 1496-501.
43. Vogtlin, A. et al., Quantification of feline herpesvirus 1 DNA in ocular fluid samples of clinically diseased cats by real-time TaqMan PCR. J Clin Microbiol, 2002. 40(2): pp. 519-23.
44. Benzekri, R. et al., Anti HSV-2 activity of *Peganum harmala* (L.) and isolation of the active compound. Microb Pathog, 2018. 114: pp. 291-298.
45. Fields B N, K. D., Howley P M, *Fields virology. 6th ed.*, ed. W. K. Health/Lippincott and W. Wilkins. 2013.
46. Ohlinger, V. F., B. Haas, and H. J. Thiel, *Rabbit hemorrhagic disease (RHD): characterization of the causative calicivirus*. Vet Res, 1993. 24(2): pp. 103-16.
47. Bank-Wolf, B. R., M. Konig, and H. J. Thiel, *Zoonotic aspects of infections with noroviruses and sapoviruses*. Vet Microbiol, 2010. 140(3-4): pp. 204-12.
48. Hurley, K. E. et al., An outbreak of virulent systemic feline calicivirus disease. J Am Vet Med Assoc, 2004. 224(2): pp. 241-9.
49. Radford, A. D. et al., Feline calicivirus infection. ABCD guidelines on prevention and management. J Feline Med Surg, 2009. 11(7): pp. 556-64.
50. Dawson, S. et al., Acute arthritis of cats associated with feline calicivirus infection. Res Vet Sci, 1994. 56(2): pp. 133-43.
51. Reubel, G. H., D. E. Hoffmann, and N.C. Pedersen, *Acute and chronic faucitis of domestic cats. A feline calicivirus-induced disease*. Vet Clin North Am Small Anim Pract, 1992. 22(6): pp. 1347-60.
52. TerWee, J. et al., *Comparison of the primary signs induced by experimental exposure to either a pneumotrophic or a 'limping' strain of feline calicivirus*. Vet Microbiol, 1997. 56(1-2): pp. 33-45.
53. Arias, A. et al., *Norovirus Polymerase Fidelity Contributes to Viral Transmission In Vivo*. mSphere, 2016. 1(5).
54. Hurley, K. F. and J. E. Sykes, *Update on feline calicivirus: new trends*. Vet Clin North Am Small Anim Pract, 2003. 33(4): pp. 759-72.
55. Coyne, K. P. et al., *Lethal outbreak of disease associated with feline calicivirus infection in cats*. Vet Rec, 2006. 158(16): pp. 544-50.
56. Pedersen, N.C. et al., An isolated epizootic of hemorrhagic-like fever in cats caused by a novel and *highly virulent* strain *of feline calicivirus*. Vet Microbiol, 2000. 73(4): pp. 281-300.
57. Reynolds, B. S. et al., *A nosocomial outbreak of feline calicivirus associated virulent systemic disease in France*. J Feline Med Surg, 2009. 11(8): pp. 633-44.
58. Schulz, B. S. et al., *Two outbreaks of virulent systemic feline calicivirus infection in cats in Germany*. Berl Munch Tierarztl Wochenschr, 2011. 124(5-6): pp. 186-93.
59. Wu, H. et al., *Antiviral effect of lithium chloride on feline calicivirus in vitro*. Arch Virol, 2015. 160(12): pp. 2935-43.
60. McDonagh, P. et al., *Antiviral effect of mefloquine on feline calicivirus in vitro*. Vet Microbiol, 2015. 176(3-4): pp. 370-7.
61. Povey, R. C., *Effect of orally administered ribavirin on experimental feline calicivirus infection in cats*. Am J Vet Res, 1978. 39(8): pp. 1337-41.
62. Stuart, A. D. and T. D. Brown, *Alpha2, 6-linked sialic acid acts as a receptor for Feline calicivirus*. J Gen Virol, 2007. 88(Pt 1): pp. 177-86.
63. Chander Y, T. A., Sajja S, Ramakrishnan M A, Faaberg K S, Goyal S M, *A TaqMan RT-PCR Assay for the Detection of Feline calicivirus*. International Journal of Virology, 2007. 3(3): pp. 100-106.

SEQUENCE LISTING

```
<160> NUMBER OF SEQ ID NOS: 6

<210> SEQ ID NO 1
<211> LENGTH: 20
<212> TYPE: DNA
<213> ORGANISM: artificial
<220> FEATURE:
<223> OTHER INFORMATION: Forward primer

<400> SEQUENCE: 1
agaggctaac ggaccatcga                                               20

<210> SEQ ID NO 2
<211> LENGTH: 19
<212> TYPE: DNA
<213> ORGANISM: artificial
<220> FEATURE:
<223> OTHER INFORMATION: Reverse primer

<400> SEQUENCE: 2
gcccgtggtg gctctaaac                                                19

<210> SEQ ID NO 3
<211> LENGTH: 35
<212> TYPE: DNA
<213> ORGANISM: artificial
<220> FEATURE:
<223> OTHER INFORMATION: Probe

<400> SEQUENCE: 3
tatatgtgtc caccaccttc aggatctact gtcgt                              35

<210> SEQ ID NO 4
<211> LENGTH: 15
<212> TYPE: DNA
<213> ORGANISM: artificial
<220> FEATURE:
<223> OTHER INFORMATION: forward primer

<400> SEQUENCE: 4
caacctgcgc taacg                                                    15

<210> SEQ ID NO 5
<211> LENGTH: 19
<212> TYPE: DNA
<213> ORGANISM: artificial
<220> FEATURE:
<223> OTHER INFORMATION: reverse primer
<220> FEATURE:
<221> NAME/KEY: misc_feature
<222> LOCATION: (6)..(6)
<223> OTHER INFORMATION: y means C or T

<400> SEQUENCE: 5
tcccayacag ttccaaatt                                                19

<210> SEQ ID NO 6
<211> LENGTH: 26
<212> TYPE: DNA
<213> ORGANISM: artificial
<220> FEATURE:
<223> OTHER INFORMATION: probe
<220> FEATURE:
<221> NAME/KEY: misc_feature
<222> LOCATION: (9)..(9)
<223> OTHER INFORMATION: y means C or T
<220> FEATURE:
<221> NAME/KEY: misc_feature
```

```
<222> LOCATION: (21)..(21)
<223> OTHER INFORMATION: y means C or T

<400> SEQUENCE: 6
cttaaatayt atgattggga yeccca                                    26
```

The invention claimed is:

1. A method for treating or preventing cat flu, comprising administering to a subject in need thereof a sulphonated polystyrene derivative of formula I:

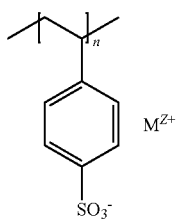

(Formula I)

wherein M is a metal cation, z is an integer from 1 to 3, n is an integer in the range of 7 to 6000, for use in the treatment and/or prophylaxis of cat flu, especially infection caused by feline calicivirus or feline herpesvirus.

2. The method of claim 1, wherein the cat flu is an infection caused by feline calicivirus.

3. The method of claim 1, wherein the cat flu is an infection caused by feline herpesvirus.

4. The method of claim 1, wherein the cat flu is an infection caused by feline herpesvirus type 1 (FHV-1).

5. The method of claim 1, wherein the cat flu of the subject is treated.

6. The method of claim 1, wherein the likelihood of developing cat flu by the subject is reduced.

7. The method of claim 1, wherein the sulfonated polystyrene derivative is in the form of a salt.

8. The method of claim 7, wherein the sulfonated polystyrene derivative is in the form of a sodium salt.

9. The method of claim 1, wherein the sulfonated polystyrene derivative has a molecular weight of at least 1.5 kDa.

10. The method of claim 1, wherein the sulfonated polystyrene derivative has a molecular weight of at least 8 kDa.

11. The method of claim 1, wherein the sulfonated polystyrene derivative has a molecular weight of from 8 kDa to 1200 kDa.

12. The method of claim 1, wherein the sulfonated polystyrene derivative has a molecular weight selected from the group consisting of 8 kDa, 19.3 kDa, 35 kDa, 46 kDa, 93.5 kDa, 200 kDa, 400 kDa, 780 kDa and 1200 kDa.

13. The method of claim 1, wherein the sulfonated polystyrene derivative has a molecular weight selected from the group consisting of 93.5 kDa and 780 kDa.

14. The method of claim 1, wherein the sulfonated polystyrene derivative is administered as a combination therapy together with a second agent for the treatment of cat flu.

15. The method of claim 14, wherein the second agent is a nucleoside analogue.

16. The method of claim 15, wherein the nucleoside analogue is acyclovir (ACV).

17. The method of claim 15, wherein the nucleoside analogue is penciclovir (PCV).

18. The method of claim 15, wherein the nucleoside analogue is acyclovir (ACV) and penciclovir (PCV).

* * * * *